US009330490B2

(12) United States Patent
Weersink et al.

(10) Patent No.: US 9,330,490 B2
(45) Date of Patent: May 3, 2016

(54) METHODS AND SYSTEMS FOR VISUALIZATION OF 3D PARAMETRIC DATA DURING 2D IMAGING

(75) Inventors: Robert Weersink, Toronto (CA); David A. Jaffray, Etobicoke (CA); Jimmy Qiu, Toronto (CA); Andrew Hope, Toronto (CA); John Cho, Etobicoke (CA); Michael B. Sharpe, Mississauga (CA)

(73) Assignee: UNIVERSITY HEALTH NETWORK, Toronto, Ontario (CA)

( * ) Notice: Subject to any disclaimer, the term of this patent is extended or adjusted under 35 U.S.C. 154(b) by 603 days.

(21) Appl. No.: 13/456,967

(22) Filed: Apr. 26, 2012

(65) Prior Publication Data

US 2013/0113802 A1 May 9, 2013

Related U.S. Application Data

(60) Provisional application No. 61/480,534, filed on Apr. 29, 2011.

(51) Int. Cl.
*G06T 15/20* (2011.01)
*A61B 6/03* (2006.01)
*G06T 19/00* (2011.01)
(Continued)

(52) U.S. Cl.
CPC . *G06T 15/20* (2013.01); *A61B 6/03* (2013.01); *A61N 5/1065* (2013.01); *A61N 5/1071* (2013.01); *G06T 19/00* (2013.01); *A61B 6/032* (2013.01); *A61B 6/037* (2013.01); *A61B 6/5247* (2013.01); *A61B 6/542* (2013.01); *A61N 5/1002* (2013.01); *A61N 2005/1074* (2013.01); *G06T 2210/41* (2013.01); *G06T 2219/008* (2013.01)

(58) Field of Classification Search
CPC ......... G06T 15/08; G06T 17/00; G06T 19/00; A61B 1/00009; A61B 19/5244; A61B 19/26; A61B 1/041; A61B 2018/00982; A61B 2019/2253
See application file for complete search history.

(56) References Cited

U.S. PATENT DOCUMENTS

| 5,283,837 A * | 2/1994 | Wood ............................ 382/285 |
| 2002/0109684 A1 * | 8/2002 | Repin et al. ................... 345/424 |

(Continued)

OTHER PUBLICATIONS

Yim, Yeny, et al. "Registration of 3D CT Data to 2D Endoscopic Image using a Gradient Mutual Information based Viewpoint Matching for Image-Guided Medialization Laryngoplasty." JCSE 4.4 (2010): 368-387.*

(Continued)

*Primary Examiner* — Ming Hon
*Assistant Examiner* — Sarah Le
(74) *Attorney, Agent, or Firm* — Norton Rose Fulbright Canada LLP; Maya Medeiros

(57) ABSTRACT

Methods and systems for visualization of 3D parametric data in a 2D image. The set of 3D parametric data includes a plurality of voxels in 3D space each associated with at least one parametric value, and the set of 2D image data includes information about a known camera position and a known camera orientation at which the 2D image was obtained. A graphical representation is generated of the parametric values of the voxels corresponding to a viewing surface in 3D space. A virtual 2D view of the viewing surface is determined. The 2D image is displayed registered with the graphical representation of the parametric values of the voxels corresponding to the virtual 2D view.

25 Claims, 10 Drawing Sheets

(51) Int. Cl.
    *A61N 5/10*     (2006.01)
    *A61B 6/00*     (2006.01)

(56) References Cited

U.S. PATENT DOCUMENTS

2007/0013710 A1* 1/2007 Higgins et al. ............... 345/581
2010/0268067 A1* 10/2010 Razzaque et al. ............. 600/424

OTHER PUBLICATIONS

Potesil, Vaclav, Xiaolei Huang, and Xiang Sean Zhou. "Automated tumor delineation using joint PET/CT information." Medical Imaging. International Society for Optics and Photonics, 2007.*
Slomka, Piotr J., et al., NPL, "Automated 3-dimensional registration of stand-alone 18F-FDG whole-body PET with CT." Journal of Nuclear Medicine 44.7 (2003): 1156-1167.*
M. Caversaccio, J. G. Giraldez, R. Thoranaghatte, G. Zheng, P. Eggli, L. P. Nolte, and M. A. G. Ballester, M. A. G., Rhinology 46, 156-158 (2008).
M. P. Fried, S. R. Parikh, and B. Sadoughi, Laryngoscope 118, 1287-1292 (2008).
W. E. Higgins, J. P. Helferty, K. K. Lu, S. A. Merritt, L. Rai, and K. C. Yu, Computerized Medical Imaging and Graphics 32, 159-173 (2008).
B. Emami, J. Lyman, A. Brown, L. Coia, M. Goitein, J. E. Munzenrider, B. Shank, L. J. Solin, and M. Wesson, International Journal of Radiation Oncology Biology Physics 21, 109-122 (1991).
S. M. Bentzen, L. S. Constine, J. O. Deasy, A. Eisbruch, A. Jackson, L. B. Marks, R. K. Ten Haken, and E. D. Yorke, International Journal of Radiation Oncology Biology Physics 76, S3-S9 (2010).
N. C. Atuegwu and R. L. Galloway, Physics in Medicine and Biology 53, 4355-4368 (2008).
J. Hummel, W. Birkfellner, T. Figl, C. Haider, R. Hanel, and H. Bergmann, Medical Imaging 2002: Visualization, Image-Guided Procedures, and Display 4681, 94-99 (2002).
P. Reittner, M. Tillich, W. Luxenberger, R. Weinke, K. Preidler, W. Kole, H. Stammberger, and D. Szolar, European Radiology 12, 592-596 (2002).
A. Khoury, J. H. Siewerdsen, C. M. Whyne, M. J. Daly, H. J. Kreder, D. J. Moseley, and D. A. Jaffray, Computer Aided Surgery 12, 195-207 (2007).
M. Daly, J. Siewerdsen, D. Moseley, Y. Cho, S. Ansell, G. Wilson, and D. Jaffray, Medical Physics 34, 2635-2635 (2007).
B. T. Phong, Communications of the Acm 18, 311-317 (1975).
W. E. Lorensen and C. H. E., Computer Graphics 21, 163-169 (1987).
S. M. Zhou, L. B. Marks, G. S. Tracton, G. S. Sibley, K. L. Light, P. D. Maguire, and M. S. Anscher, Medical Physics 27, 1727-1731 (2000).
G. J. Meijer, M. Van Den Brink, M. S. Hoogeman, J. Meinders, and J. V. Lebesque, International Journal of Radiation Oncology Biology Physics 45, 1073-1080 (1999).
P. D. Maguire, G. S. Sibley, S. M. Zhou, T. A. Jamieson, K. L. Light, P. A. Antoine, J. E. Herndon, M. S. Anscher, and L. B. Marks, L. B., International Journal of Radiation Oncology Biology Physics 45, 97-103 (1999).
S. D. Li, A. Boyer, Y. Lu, and G. T. Y. Chen, Medical Physics 24, 1107-1116 (1997).
Y. Lu, S. S Li, D. D Spelbring, P. Song, S. Vijayakumar, C. Pelizzari, and G. T. Y. Chen, Medical Physics 22, 279-284 (1995).
R. Munbodh, A. Jackson, J. Bauer, C. R. Schmidtlein, and M. J. Zelefsky, Medical Physics 35, 2137-2150 (2008).
M. Werner-Wasik, E. Yorke, J. Deasy, J. Nam, and L. B. Marks, International Journal of Radiation Oncology Biology Physics 76, S86-S93 (2010).
T. Rancati, M. Schwarz, A. M. Allen, F. Feng, A. Popovtzer, B. Mittal, and A. Eisbruch, International Journal of Radiation Oncology Biology Physics 76, S64-S69 (2010).
T. Rancati, C. Fiorino, and G. Sanguineti, International Journal of Radiation Oncology Biology Physics 75, 915-923 (2009).
T. Pavlidis, "The Use of a Syntactic Shape Analyzer for Contour Matching," IEEE Trans. Pattern Analysis and Machine Intelligence, PAMI-1 (1979), pp. 307-310.
T. Pavlidis, "Algorithms for Shape Analysis of Contours and Waveforms," IEEE Trans. Pattern Analysis and Machine Intelligence, PAMI-2 (1980), pp. 301-312.
P. Bourke, "Conrec: A Contouring Subroutine", Byte Magazine, 1987.
W. E. Lorensen, H. E. Cline: Marching Cubes: A high resolution 3D surface construction algorithm. In: Computer Graphics, vol. 21, Nr. 4, Jul. 1987.
T. Y. Lee, C. H. Lin, Growing-cube isosurface extraction algorithm for medical volume data, Comput Med Imaging Graph. Sep.-Oct. 2001;25(5):405-15.
C.I. Dickie; A. Griffin; A. Parent; P. Chung; C. Catton; J. Wunder; P. Ferguson; M. Sharpe; R. Bell; B. O'Sullivan, "Phase II Study of Preoperative Intensity Modulated Radiation Therapy for Lower Limb Soft Tissue Sarcoma", International Journal of Radiation Oncology, Biology, Physics (Nov. 2010), 78 (3), Supplement, p. S84-S85.

\* cited by examiner

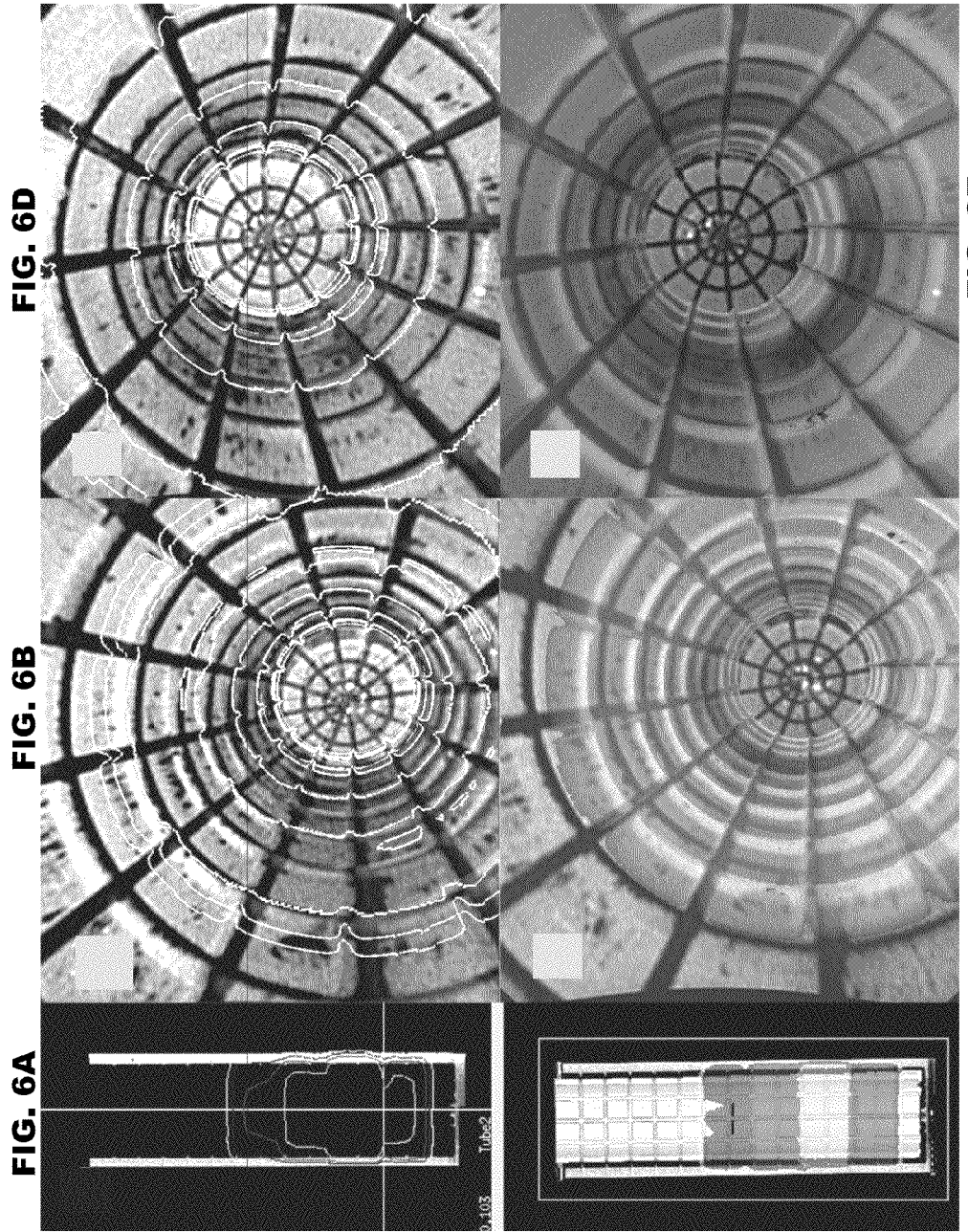

Table 1: Visualization frame rate and processing time for dose display in several test cases.

| Case | No. of Points | No. of Polygons | Frames per Second | | | Render time for Capture (ms) | |
|---|---|---|---|---|---|---|---|
| | | | Baseline | Isolines | Colorwash | Isoline | Colorwash |
| Tube Phantom | 701,202 | 1,402,340 | 10.4 | 5.3 | 3.5 | 78.8 | 126.2 |
| Skull Phantom | 816,538 | 1,632,086 | 9.1 | 4.9 | 3.0 | 89.7 | 136.7 |
| Clinical Case 1 | 1490,595 | 2,971,334 | 6.4 | 3.2 | 1.4 | 149.0 | 244.2 |
| Clinical Case 2 | 1,504,749 | 3,003,980 | 5.8 | 3.0 | 1.8 | 150.9 | 249.7 |
| Clinical Case 3 | 1,433,098 | 2,862,985 | 6.5 | 3.3 | 1.9 | 144.0 | 238.1 |

FIG. 9

METHODS AND SYSTEMS FOR VISUALIZATION OF 3D PARAMETRIC DATA DURING 2D IMAGING

CROSS-REFERENCE TO RELATED APPLICATIONS

The present disclosure claims priority from U.S. provisional patent application No. 61/480,534, filed Apr. 29, 2011, the entirety of which is hereby incorporated by reference.

TECHNICAL FIELD

The present disclosure is related to methods and systems for visualization of 3D parametric data in 2D images. In particular, the disclosed methods and systems may provide for visualization of 3D radiation dose data in real-time during 2D imaging procedures.

BACKGROUND

Medical practice has generally considered the fields of radiology (which may including imaging modalities such as computer tomography (CT), magnetic resonance imaging (MRI), positron emission tomography (PET) and X-ray imaging) and endoscopy as separate specialties. While CT and MRI may be used to provide 3D anatomical information, image acquisition typically is not in real-time and analysis of the images is typically retrospective. Endoscopy typically provides only 2D superficial information, but in real-time, with colour, contrast and texture, which may be useful for providing diagnostic information. Conventionally, endoscopy is typically performed as a separate procedure that is only qualitatively connected to 3D imaging modalities such as CT and MRI. Any spatial correlation of the information is typically made qualitatively by the clinician through comparison of common anatomical features.

Methods have been developed to enable co-visualization of the 2D images with 3D anatomical information derived from 3D images. Such methods typically been developed in the field of surgical guidance.

The registration of 2D endoscopic images with volumetric imaging has been an area of exploration and development primarily in the context of surgical guidance[1,2] and bronchoscope tracking for guiding biopsies.[3] In these cases, the endoscopy may typically serve to extend the clinician's vision into luminal organs, with tracking relating the position of the "eyes" with respect to volumetric imaging. To date, the role of endoscopy in radiation therapy may be typically limited to clinical evaluation of the tumor prior to therapy and response evaluation following therapy. This evaluation, however, may be typically independent of any 3D volumetric information except for that provided by the clinician's association of anatomical landmarks in their notes. It has been suggested that quantitative registration of endoscopy with radiation planning CT may be used as an aid in contouring superficial lesions not typically visible in volumetric imaging.

SUMMARY

The present disclosure provides methods and systems useful for representing 3D parametric information on 2D views of a real object. The disclosed methods and systems may be useful in several medical applications. Examples may include the visualization of radiation dose on endoscopic images of the head and neck, and visualization of PET positron emission tomography signal during a bronchoscopic procedure.

The present disclosure describes methods and systems for displaying volumetric data values (also referred to as 3D parametric data) registered on 2D images. In particular, the values of data points of a set of volumetric data that reside on a non-planar surface may be shown in a 2D visualization of the surface. An example application described herein is the display of 3D radiation dose on a 2D endoscopic image, for example as isodose lines on the imaged surface or as a color map, with color representing dose values.

Certain setup and registration techniques, described in PCT Publication No. WO2010/130056, which is hereby incorporated by reference in its entirety, may be suitable for the present disclosure.

In some example aspects, the present disclosure provides a method for visualization of 3D parametric data in a 2D image, the method may include: receiving signals representing a set of 3D parametric data, the set of 3D parametric data including a plurality of voxels in 3D space each associated with at least one parametric value; receiving signals representing a set of 2D image data representing the 2D image, the set of 2D image data including information about a known camera position and a known camera orientation at which the 2D image was obtained; defining a viewing surface in the 3D space; identifying voxels of the set of 3D parametric data corresponding to the viewing surface; generating a graphical representation of the parametric values of the voxels corresponding to the viewing surface; determining a virtual 2D view of the viewing surface corresponding to the known camera position and the known camera orientation of the 2D image; and providing signals for displaying the 2D image using the set of 2D image data registered with the graphical representation of the parametric values of the voxels corresponding to the virtual 2D view.

In some examples, the set of 3D parametric data may represent 3D radiation dose data and/or 3D positron emission tomography (PET) data.

In some examples, the 3D space may be defined by registration of the 3D parametric data to 3D imaging data.

In some examples, the 3D imaging data may include computed tomography (CT) imaging data.

In some examples, the 2D image may include an endoscopic image.

In some examples, there may be a plurality of 2D images that may be updated continuously or intermittently in real-time, the virtual 2D view may be updated in real-time to correspond to each update of the 2D images, and the display may be updated in real-time to display the each updated 2D image registered with the graphical representation corresponding to the updated virtual 2D view.

In some examples, the method may include determining which voxels corresponding to the viewing surface are visible at the known camera position and the known camera orientation, where voxels that are visible may be determined to be visible voxels and voxels that are not visible may be determined to be not visible voxels; and wherein the graphical representation may include only the parametric values of the visible voxels.

In some examples, the graphical representation of the parametric values may include at least one of: a set of isolines and a color map.

In some examples, the graphical representation may include a set of isolines, and generating the set of isolines may include: determining a set of isosurfaces in the 3D parametric data, each isosurface including voxels of the 3D parametric data having parametric values equal to a defined value or within a defined value range; and determining, for each isosurface, a respective intersection between that isosurface and the viewing surface, each respective intersection defining an isoline corresponding to the respective defined value or defined value range.

In some examples, the graphical representation may include a color map and generating the color map may include: generating a copy of the viewing surface having a plurality of defined regions; for each region, determining any intersection between that region and any voxels in the 3D parametric data; where there is no voxel in the 3D parametric data intersecting with that region, assign that region to be transparent; where there is at least one intersecting voxel in the 3D parametric data intersecting with that region, assign an opaque color to that region based on the parametric value of the at least one intersecting voxel; wherein any regions assigned an opaque color together define the color map.

In some examples, a threshold value may be defined for the values of the 3D parametric data, wherein any voxel associated with a parametric value that does not meet the threshold value may be rendered in a background color or may be rendered transparent in the graphical representation.

In some examples, the set of 2D image data may be displayed overlaid and/or underlaid with the graphical representation.

In some examples, the set of 2D image data may be displayed overlaid and/or underlaid with the graphical representation.

In some examples, the graphical representation of the parametric values may be provided for a selected portion of the viewing surface.

In some examples, the method may include displaying actual numerical value or values of the parametric value or values associated with a selected point or portion of the viewing surface.

In some examples, the 3D parametric data may include data representative of at least one of a surface property and a subsurface property of the viewing surface.

In some example aspects, the present disclosure provides a system for visualization of 3D parametric data in a 2D image, the system may include: a processor configured to execute computer-executable instructions to carry out the methods described above; and a display for displaying the 2D image registered with the graphical representation of the parametric values of the voxels corresponding to the virtual 2D view.

In some examples, the system may include a camera for capturing the 2D image.

In some examples, the system may be an imaging workstation.

BRIEF DESCRIPTION OF FIGURES

FIGS. 6A-6E shows examples of visualization of isodoses in a phantom using an example of the disclosed methods and systems;

FIG. 9 shows a table that provides example visualization frame rates and processing times found in example studies.

DETAILED DESCRIPTION

Figure 1:
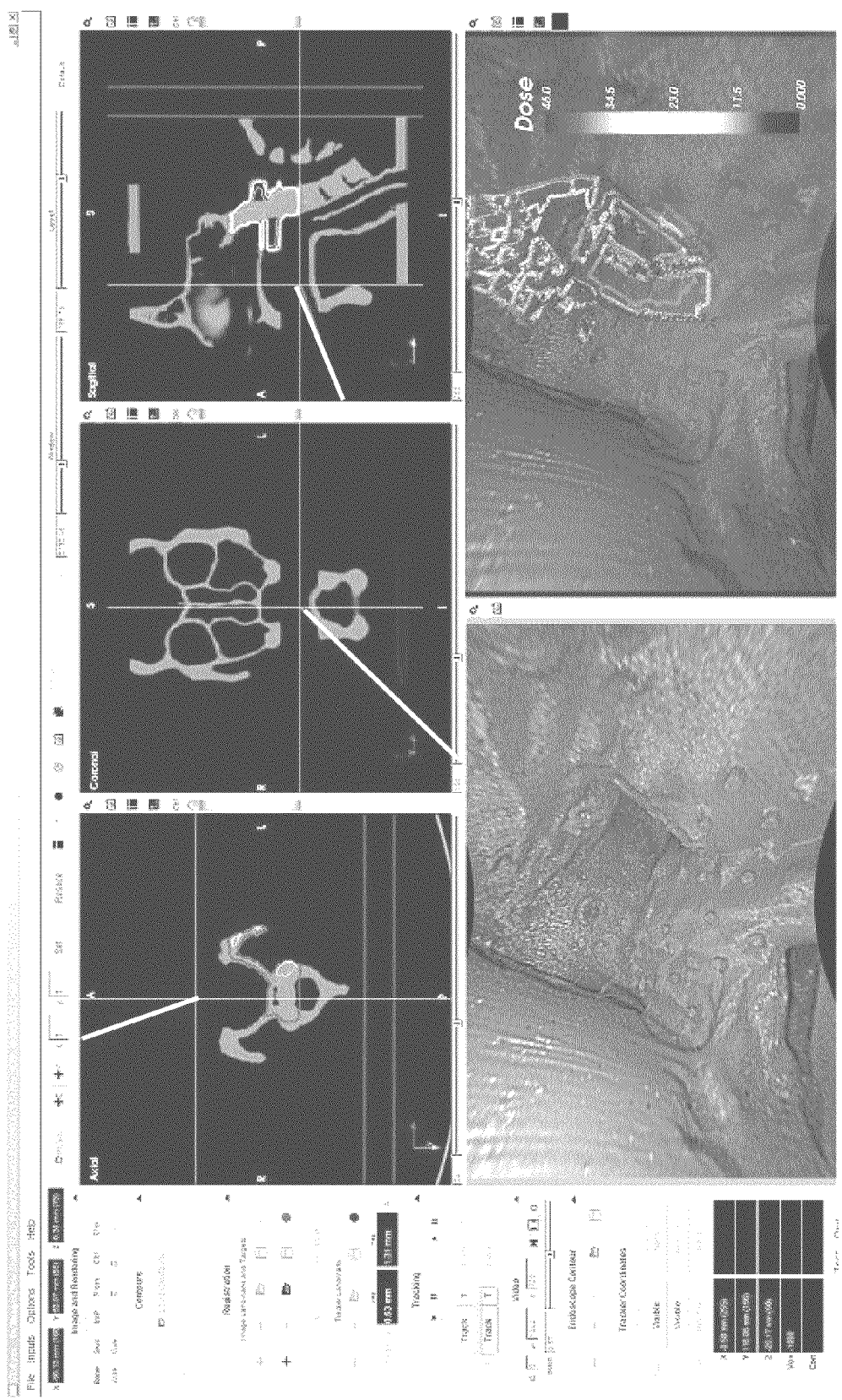
FIG. 1 shows a screen shot illustrating an example implementation of the disclosed methods and systems, using contour lines.

The display of radiation dose on endoscopic images, in radiation therapy, may serve to provide quantitative measures with respect to delivered dose when assessing tissue response. Directly relating tumor response, as observed endoscopically, to the spatially-resolved dose distribution may be useful in adaptive therapy for various endoluminal cancers. The dose display may also be useful for quantitative assessments of toxicities with delivered surface dose for various clinical complications in luminal organs such as radiation proctitis, mucositis and esophagitis, among others. Normal tissue complications may be typically assessed using dose volume approaches, such as those originally outlined by Emami[4] and more recently elaborated on with the QUANTEC group[5]. Relating clinical grading of the above conditions directly to the dose rather than volumetric measures may help to improve the clinical care of individual patients and/or improve general understanding of how these conditions arise.

Dose display in conventional radiation treatment planning platforms may be primarily limited to visualization on 2D planar slices through the 3D image volume or on virtual 3D renderings of surfaces generated from volumetric images using texture mapping techniques. A challenge with endoscopic dose display may be to present only the dose visible on the non-planar surface that is within the camera view, and additionally to continually or intermittently update this dose display. In this disclosure, visualization of radiation dose is provided as an example, however other volumetric parameter values may be likewise displayed, including, for example, PET signals, functional MRI signals, and contrast CT signals, among others.

Visualization of 3D parametric information (e.g., non-anatomical information) on a computer-generated surface rendering of an object may be possible using the disclosed methods and systems. Such parametric information may include, for example, radiation dose from a radiation treatment, thermal dose from an ablative treatment such as radio frequency ablation or photothermal therapy, or PET signals, among others. It may be useful to provide methods and systems for representing 3D parametric information on true 2D image views, for example in real-time.

The present disclosure provides methods and systems useful for representing 3D parametric information on 2D views of a real object. The disclosed methods and systems may be useful in several medical applications. Examples may include the visualization of radiation dose on endoscopic images of the head and neck, and visualization of PET positron emission tomography signal during a bronchoscopic procedure.

Endoscopy may be performed for various luminal cancers (e.g., head and neck, rectal, etc.), post-radiation treatment to assess treatment outcome and tumour regression and to grade any clinical toxicities, for example. For example, radiation-induced mucositis in head and neck cancers or radiation-induced proctitis of the colon following the treatment of prostate cancer can be examined visually using endoscopic procedures. Conventionally, comparison with actual radiation dose delivered to the tissue is only made qualitatively, typically based on anatomical landmarks common to the endoscopy procedure and the patient's CT image used in the radiation treatment planning process. Thus conventionally, direct comparisons of toxicities in patients with similar normal tissue doses typically cannot be made. The present disclosure may provide a solution for this problem.

PET provides functional information that can be used to locate the site, spread and size of cancer, and to differentiate benign from malignant disease, for example. It can be used for lung and head and neck cancers, for example. Endoscopic procedures can also be used to assess the superficial spread of disease, for example. Thus, co-visualization of the 3D PET data with the 2D real-time imaging during an endoscopy procedure, which may be an application of the present disclosure, may provide quantitative correlation of these separate diagnostic methods and may help improve disease diagnosis.

The disclosed methods and systems may be useful for visualization of 3D parametric data, such as 3D radiation dose data, in 2D images, such as 2D endoscopy images. Such 3D parametric data may be non-anatomical data, for example unlike CT or MRI image data. Such non-anatomical data may conventionally be difficult to relate to 2D images. For example, portions of the anatomy or tissue structures may partially or fully obscure the view of 3D parametric data in a 2D view. The disclosed methods and systems may allow for visualization of 3D parametric data in 2D images in real-time, for example while the 2D images are being acquired, such as in an endoscopy procedure. This may be useful compared to conventional registration of 3D parametric data in a static virtual model.

The set of 3D parametric data, such as radiation dose data, may be calculated in 3D space and displayed, in real-time, as 2D images are acquired. Further, the registration of 3D parametric data to 2D images may be registered back to a 3D space (e.g., a 3D model of the imaged surface), to generate 3D visualization of the original 3D parametric data with a 3D model of the 2D image.

Although the present disclosure describes 3D radiation dose data as an example of 3D parametric data, other 3D parametric data may be suitable, including, for example, PET data, temperature data, and other such data. Display of the 3D parametric data in 2D images may include identifying in the set of 3D parametric data those data points that correspond to regions visible in the set of one or more 2D image(s), associating the identified data points with their respective corresponding regions in the set of 2D image(s), and displaying the value of the data points in the set of 2D image(s).

The 3D parametric data may be displayed in the 2D image(s) in any suitable manner including, for example, as isolines (e.g., contours), a color map (e.g., with different colors representing different data values), or any other suitable method.

Examples of the disclosed methods and systems are now described. These examples are provided for the purposes of illustration only and are not intended to be limiting. It should be understood that variations may be made to these examples within the scope of the present disclosure.

3D Parametric Data

In some examples, the acquisition of 3D parametric data may involve first obtaining 3D imaging data. The 3D imaging data may serve as a base data set to which a video imaging system is registered. In an example application in radiation therapy, the 3D imaging data may be provided by CT imaging, which may also be used for planning a radiation dose to be delivered to a patient.

The 3D parametric data may be any suitable set of information or data points in 3D space. Examples include radiation dose (e.g., planned or delivered), PET signal, blood perfusion, exogenous agent distribution, and any other suitable 3D parametric data. The parameter values may be calculated in relation to the 3D imaging data, in order to relate the parametric data to 3D space. The format for this may be a 3D grid of parametric data values, relating each data point in the set of parametric data to a respective 3D spatial coordinate.

For example, in the application of radiation therapy, for radiation dose, the dose grid may be calculated in any suitable radiation treatment planning system and/or radiation dose calculation software. The dose grid may be exported from the software used to calculate the radiation dose. In the present example, the dose grid is calculated using Pinnacle (Philips). Such a dose grid may then be related to CT imaging data.

In some examples, the set of 3D parametric data may already be provided and may already be related to a 3D space or a set of 3D imaging data, and the above steps may not be necessary.

Example System

In some examples, the set of 2D image data may be obtained using any suitable imaging device (e.g., any visible light imaging device) as a camera for the disclosed system. For example, a video recording device may be used. Other suitable examples may include a video camera, endoscope, thermal imaging camera, or any other imaging device that may provide a surface view of a region of interest of the patient. In the example system described here, the camera may be provided by a flexible endoscope. In other examples other cameras may be used, including both video and static cameras.

The position and/or orientation of the camera relative to the 3D imaging data (or any other suitable defined 3D space) may be tracked. Any suitable tracking device or tracking method (e.g., tracking software) that can track the position and/or orientation of the camera relative to the 3D imaging data may be used. Examples of suitable tracking devices may include optical sensors, electromagnetic sensors, accelerometers, and other such devices. Examples of suitable tracking methods may include the use of image landmarks, mutual information techniques, and other such techniques capable of deriving the camera position and/or orientation relative to the volumetric image. Such tracking methods may be implemented by any suitable one or more software application(s). In some examples, a combination of two or more tracking devices and/or methods may be used to track the camera. For example, one device may track the position of the camera while another device may track the orientation of the camera. In the example system described here, miniature electromagnetic sensors may be used. These sensors may be placed within the working channel of a flexible endoscope providing an endoscopic camera.

Example of Registration of 3D Parametric Data to 2D Image Data

Figure 3A:
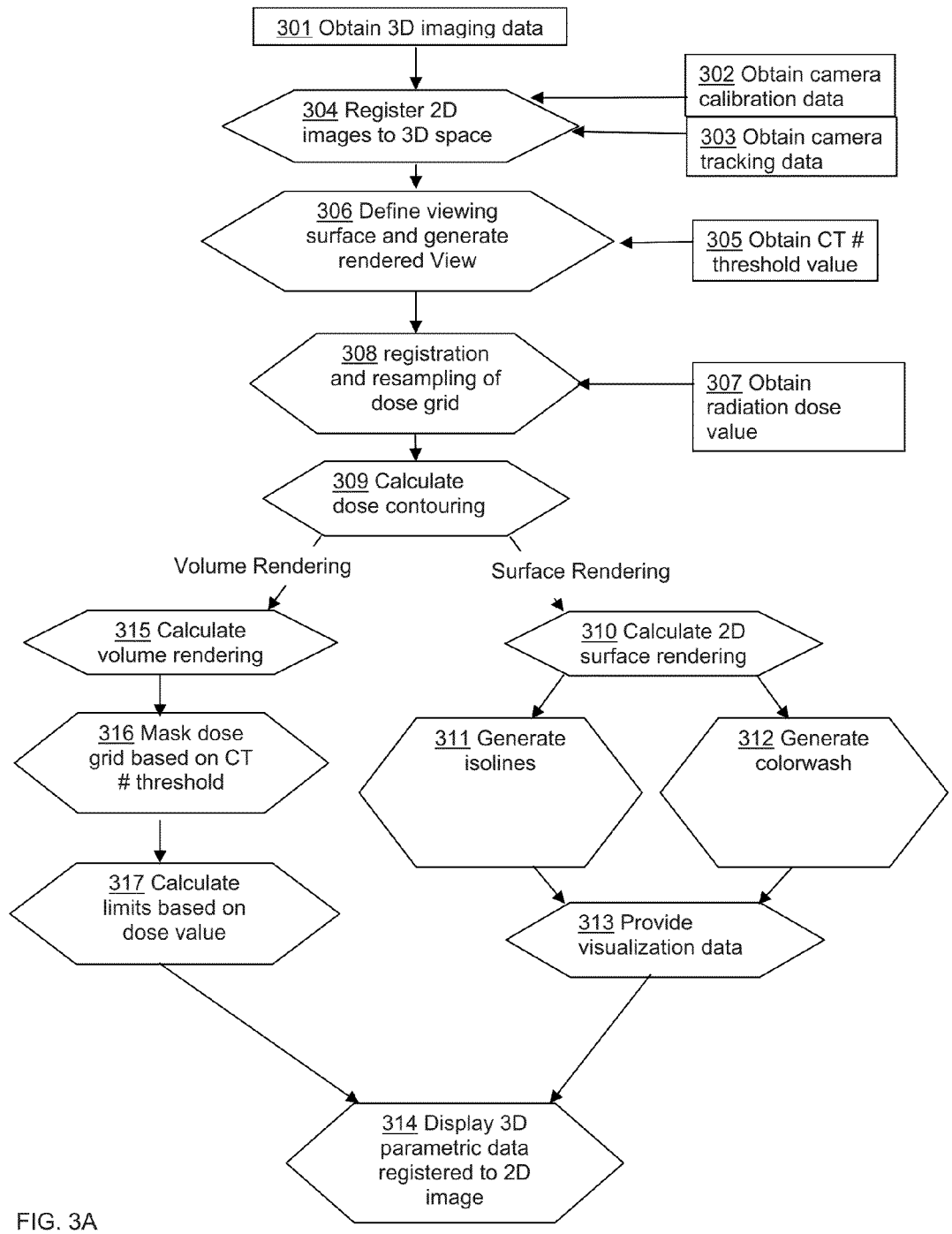
FIGS. 3A and 3B are flowcharts illustrating example methods for generating a visualization of 3D parametric data during 2D imaging.
Figure 3B:
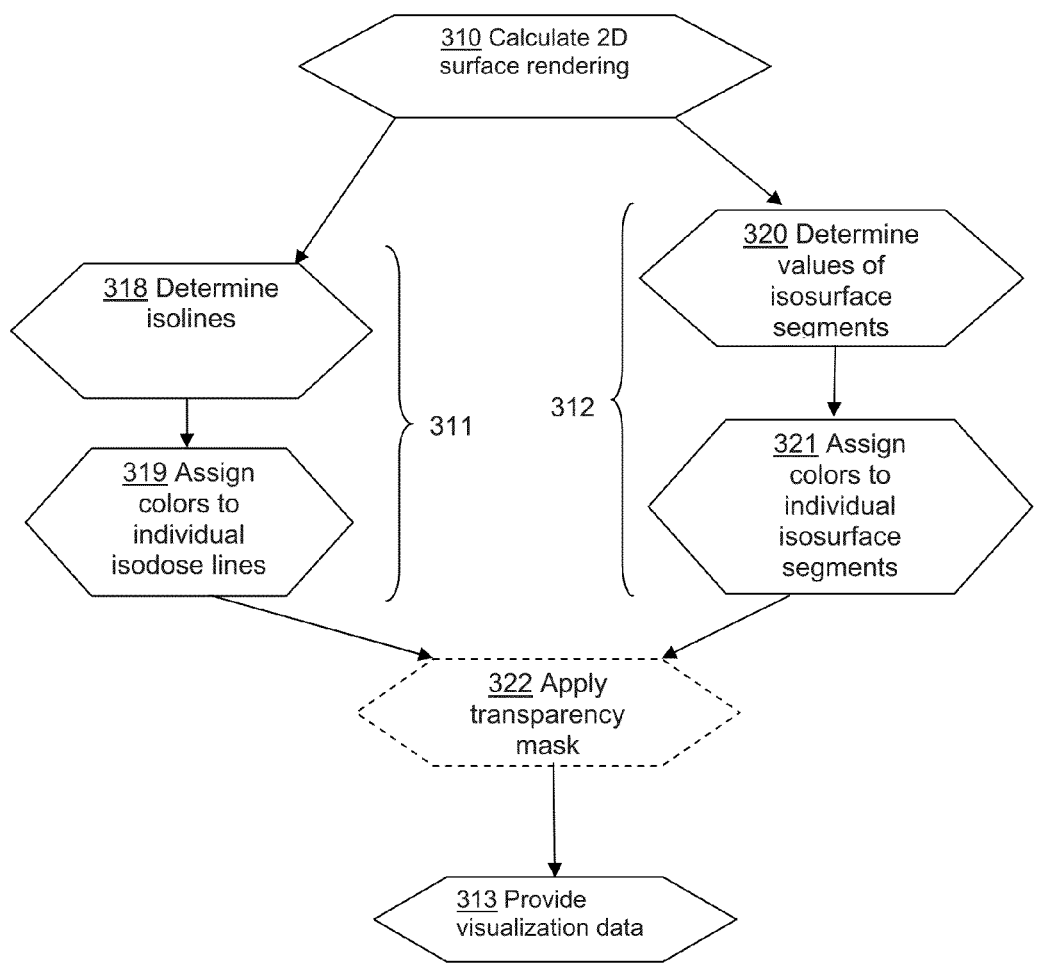

A flowchart for an example of the disclosed methods is shown in FIGS. 3A and 3B.

Reference is first made to FIG. 3A.

At 301, a set of 3D imaging data may be obtained, for example as described above.

At 302 and 303, sets of calibration data and tracking data for a 2D camera may be obtained, for example using one or more sensors as described above.

At 304, a set of 2D image data obtained from the camera may be registered to the 3D space defined by the 3D imaging data. This may include registering both data sets together into a common coordinate space, using suitable coordinate tracking methods.

At 305, a CT # threshold value may be obtained. This may be a pre-defined value or may be obtained from user input, for example. This threshold value may be used to separate tissues, such as soft tissues or bone, from the rest of the CT image (e.g., air, fluids and/or signal noise), in order to define a 3D surface or volume of interest. The threshold value may be adjusted (e.g., manually by a user) as appropriate to exclude certain CT signals. In examples where the 3D imaging data is other than CT imaging data, other methods of defining a surface or volume of interest may be used, as appropriate. For example, the viewing surface may be defined by the imaged air-tissue interface At 306, a viewing surface in 3D space may be defined (e.g., using the CT # threshold value) and a rendered view of the viewing surface may be generated, based on the set of 3D imaging data. The viewing surface may provide the 3D location of the 2D surface that is being imaged by the camera (e.g., using the registration at 304). The viewing surface may be defined, for example, using a set of polygons (e.g., triangles and/or quadrilaterals) in 3D space. The size of such polygons may define the granularity of the viewing surface.

The viewing surface may also be used to define a subset of the set of 3D parametric data that is to be visualized. For example, where the set of 3D parametric data provides information for a larger volume than that spanned by the viewing surface, only a subset of the 3D parametric data corresponding to the volume spanned by the viewing surface may be of interest and the rest of the 3D parametric data may be excluded from further consideration.

The viewing surface may be set to a background color (e.g., a color similar to the color of the actual tissue in the 2D view) or a mask color that may be used for transparency rendering (e.g., a color not assigned to a parametric value on the colorscale), as described further below.

At 307, a set of 3D parametric data may be obtained. In this example, the set of 3D parametric data is radiation (RT) dose data. Such data may be obtained using any suitable method, for example as described above. Although this is shown as step 307, the set of 3D parametric data may be obtained at any point earlier in the method, as appropriate.

At 308, the set of 3D parametric data may be registered to the defined viewing surface. If necessary, in the example of 3D radiation dose data, resampling of the dose grid is performed. Such resampling may be appropriate, for example, where the set of 3D radiation dose data does not match the volume spanned by the viewing surface and/or does not match the granularity or resolution of the viewing surface.

At 309, contours of the 3D parametric data may be calculated for the defined viewing surface. The calculated contours may be used for surface rendering (e.g., in the set of 2D imaging data) and/or volume rendering (e.g., in the set of 3D imaging data). In some examples, isosurface segments of the viewing surface may be generated. Isosurface segments may be defined as segments of the 3D viewing surface associated with respective sets of data having the same or similar parametric values or value ranges. Each isosurface segment may be assigned a respective parametric value (e.g., a value, such as an average or a median, representative of the values or value ranges of the sets of data associated with that isosurface segment).

For surface rendering, at 310, a 2D surface rendering may be calculated for the 3D viewing surface. This may involve projecting or aligning the 3D viewing surface with a 2D image of interest from the set of 2D image data. An example of surface rendering is described in further detail with respect to FIGS. 4A-4D, below. Values of the 3D parametric data (e.g., dose scalars, in the case where the parametric data is dose data) may be assigned to individual isosurface segments. The surface rendering may be rendered as isolines, in which case the method may continue at 311, or as a colorwash, in which case the method may continue at 312. In some examples, both isolines and the colorwash may be calculated (i.e., both 311 and 312 may be carried out). The user may be provided with an option for selecting one or the other, or for toggling between display of one or the other, or for displaying both together.

At 311, isolines may be rendered, as described further below. Where the disclosed methods and systems are used for rendering visualization of dose data (e.g., radiation dose data), isolines may also be referred to as isodose lines or isodose.

At 312, a colorwash (which may be also referred to as a colormap) may be rendered, as described further below.

At 313, the isoline and/or colorwash data calculated in the previous steps may be provided for visualization. For example, colored isoline and/or colorwash data may be stored for future displaying and/or may be transmitted to another processor for further processing, storing and/or displaying and/or may be used for immediate displaying.

FIG. 3B further illustrates examples of the surface rendering.

For example, for rendering of isolines, carrying out 311 as described above may include:

At 318, isolines may be determined. This may involve identifying points on the 3D surface that are associated with a respective sets of data having the same or similar parametric values or value ranges, and connecting those points to define a contour line for that predefined value or value range. Isolines may also be generated using 3D marching cubes on the 3D surface, as will be described further below, to extract isoline bands and/or edges.

Isolines may also be generated by calculating intersections of isosurfaces in the 3D parametric data with the rendered viewing surface. Isosurfaces in the 3D parametric data may be defined by respective sets of data having the same or similar values or value ranges. For example, in the case of 3D radiation dose data, all data having radiation dose values within a defined range may be considered to have similar dose values, and the 3D location of these data points together may define an isosurface for the defined range of values. Such intersections may be used to determine isolines or contours on the viewing surface.

At 319, a respective color may be assigned to each generated isoline. For example, a colorscale of parametric values may be defined (e.g., preset by default or set by the user), and colors may be assigned to each generated isoline corresponding to the value or value range defined for that isoline.

A set of color values may be calculated for the 3D parametric data values. This may assign certain colors to certain values of the isolines determined above. For example, in the case of 3D dose data, certain colors may be assigned to certain dose or isodose values. This may provide a colored set of isolines for the viewing surface. Regions of the data having no dose, or outside the range of defined dose values, may be colorless or transparent.

The user may be provided with an option to set threshold values (e.g., minimum and/or maximum values) for displaying parametric data, where values that do not meet the threshold (e.g., lower than the set minimum value and/or higher than the set maximum value) are not assigned a color on the colorscale. The user may also be provided with options for adjusting the colorscale (e.g., selecting grayscale or full color, or selecting the range of colors used in the colorscale).

For rendering of a colorwash, carrying out 312 may include, for example:

At 320, if not already done (e.g., at 309 described above), the parametric value associated with each isosurface segments of the 3D surface may be determined. For example, in the case of 3D radiation dose data, all data having radiation dose values within a defined range may be considered to have similar dose values, and the 3D location of these data points together may define an isosurface for the defined range of values.

At 321, a respective color may be assigned to each isosurface segment. For example, a colorscale of parametric values may be defined (e.g., preset by default or set by the user), and colors may be assigned to each isosurface segment corresponding to the value or value range defined for that isosurface segment.

A set of color values may be calculated for the 3D parametric data values. This may assign certain colors to certain values of the isosurface segments determined above. For example, in the case of 3D dose data, certain colors may be assigned to certain dose or isodose values. This may provide a colored set of isosurface segments for the viewing surface. Regions of the data having no dose, or outside the range of defined dose values, may be colorless or transparent.

The user may be provided with an option to set threshold values (e.g., minimum and/or maximum values) for displaying parametric data, where values that do not meet the threshold (e.g., lower than the set minimum value and/or higher than the set maximum value) are not assigned a color on the colorscale. The user may also be provided with options for adjusting the colorscale (e.g., selecting grayscale or full color, or selecting the range of colors used in the colorscale).

At 322, optionally a transparency mask may be applied to the generated isolines and/or the colorwash. The transparency mask may cause any portions of the 3D surface that is not assigned a color on the colorscale to be rendered transparent. For example, any portions of the surface that is below a defined minimum parametric value (e.g., below a minimum dose level) may be rendered transparent. An example of this transparency mask is described further below.

Reference is again made to FIG. 3A.

For volume rendering, at 315, a volume rendering of the 3D imaging data may be calculated. This may be based on the 3D surface or volume of interested determined previously using the CT # threshold value.

At 316, a mask of the 3D parametric data (e.g., 3D dose grid) may be performed based on the CT # threshold value. For example, parametric data corresponding to points in space outside of the surface or volume of interested, as determined using the CT # threshold, may be excluded from further consideration.

At 317, limits on the 3D parametric data may be calculated. For example, where the 3D parametric data is 3D radiation dose data, limits based on the dose value may be calculated and/or adjusted. For example, data having values outside of a defined range may be excluded. In some examples, certain colors may be assigned to certain parametric values, in order to generate a color map that may be registered and overlaid and/or underlaid on the volume rendering. If necessary, transparency of the color map may be adjusted for display. Optionally, the color map may be stored for future displaying and/or transmitted to another processor for further processing, storage and/or displaying and/or may be used for immediate displaying.

At 314, the surface rendering and/or volume rendering data may be displayed as an overlay and/or underlay registered to one or more 2D images. This display may be provided by a conventional display of an imaging workstation, for example. If necessary, transparency of the surface rendering and/or volume rendering data may be adjusted for suitable display. In some examples, this display may be updated in real-time as the 2D image(s) is updated in real-time (e.g., in a video display). Where appropriate, any of the steps described above may be repeated, for example to re-register a new 2D image to the 3D space.

In some examples, the example method of FIGS. 3A and 3B need not be carried out in its entirety. For example, volume rendering may not be carried out and steps 315-317 may be omitted. For example, registration of the set of 2D imaging data to the set of 3D imaging data may be already performed and steps 301-304 may be omitted. For example, the viewing surface may have been pre-defined and steps 305-306 may be omitted. Other variations may be possible.

Although the method has been described as rendering parametric data for all of the viewing surface (where values meet threshold requirements, if applicable), in some examples the user may be provided with options for defining one or more portions of the viewing surface for which parametric data should be rendered. For example, the user may be interested in data only for a portion of the viewing surface (e.g., corresponding to a treatment area of interest) and the user may select that portion only (e.g., using highlighting, by defining a boundary or other selection methods, using any suitable input means such as mouse, keyboard, touchscreen or trackball, for example). A rendering of the parametric data may then be displayed only for that selected portion. Where a portion of the viewing surface has been selected for displaying rendered parametric data, rendering of the parametric data may only be carried out for that selected portion, or rendering may nonetheless be carried out for the entire viewing surface (e.g., in order to avoid re-processing should the user later select a different portion of the viewing surface to view).

In some examples, the user may also be provided with an option to view the actual numerical value of the parametric data for one or more points or portions of the viewing surface. For example, the user may select a portion or point on the viewing surface (e.g., by clicking on a point in the display using a mouse, or by defining a coordinate using a keyboard, or any other suitable input method) and the actual numerical value of the parametric data associated with that point (or the next closest point associated with a parametric data point, or a calculated estimate of the parametric data at the selected point) on the viewing surface may be displayed (e.g., as a pop-up window, as a label, or using any other suitable display methods).

Although the parametric data may be rendered to be displayed as an overlay/underlay on a viewing surface, the parametric data may not be associated with the surface. For example, the parametric data may be associated with a subsurface property (e.g., for viewing subsurface radiation dosage), a combination of surface and subsurface properties, or any other suitable parametric data.

Example Studies

Example studies are now described, in which an example of the disclosed methods and systems is implemented using a set of CT imaging data as the set of 3D imaging data, radiation dose values as the set of 3D parametric data, electromagnetic (EM) tracking devices for coordinate tracking of the 2D camera and a flexible endoscope to provide the camera. In these examples, the EM tracking devices are attached to the tip of the flexible endoscope so that the position and orientation of the endoscope tip (at or near where the camera is located) may be tracked. Details of the example tracking and registration steps are described in the examples below.

Example 1

Setup

In this example study, a software application written in C++ and developed using VTK (Visual Toolkit; http://www.vtk.org/) and IGSTK (Image Guided Surgery Toolkit; http://www.igstk.org/) toolkits may be used. An earlier version of this software has been used for image-guided surgical procedures (see, for example[9,10]). Such open source toolkits may provide algorithms for image data processing and visualization, tool tracking and/or rigid registration in the present example.

EM tracking devices are used in this example to track the coordinates of a flexible endoscope tip (which provides the camera in this example). In this example, the EM devices are cylindrical EM sensors (5 mm long, 1.5 mm diameter) (Aurora, Northern Digital, Waterloo, Ontario, Canada), which provide 6 degrees of freedom (DoF) (x, y, z, pitch, yaw, roll). The sensors may be drawn through the working channel of a flexible bronchoscope (Evis Extera II Gastrointestinal Videoscope, Olympus, Canada) and fixed in place, for example using thin shrink wrap around the exterior of the bronchoscope. All 6 DOFs may be used to track the position and orientation of the 2D endoscopic imaging data within the set of 3D CT imaging data in real-time.

Calibration of the camera, in this example an endoscope camera, may involve determining parameters that may be commonly classified as either intrinsic or extrinsic. Intrinsic parameters are typically those specific to the optical collection system, such as camera focus, principal point, skew and distortion. Extrinsic parameters typically relate the camera position with respect to the EM sensor and hence to the real-world coordinate reference frame. In this example, camera calibration was performed using the Camera Calibration Toolbox (http://www.vision.caltech.edu/bouguetj/calib_doc/index.html) in MatLab, modified to export the camera spatial coordinates. Ten representative endoscopic images from several random positions and orientations were acquired of a black and white 10×10 square checkerboard with each block 5 mm in length. Corners were automatically identified in each image using standard image analysis tools. Comparison of these input points with the actual positions of the points, derived from the known dimensions of the grid, was then used to calculate the camera's intrinsic parameters. The calibration process also determined the camera coordinates (i.e., position and orientation) for each calibration image. These coordinates were compared to the corresponding coordinates of the EM sensor measured for each image to register the camera coordinate system with that of the EM sensors. This process provided the camera's extrinsic parameters.

Once the calibration model was derived, a pixel-to-pixel mapping procedure may be used to transfer the original video image obtained from the camera into a relatively distortion-free 2D image. Within the calibration software used in this example, such optical correction may be performed by mapping the distortion-corrected endoscopic image in real-time to an image plane in VTK. This may enable overlay and/or underlay of the geometrically corrected endoscopic feed with the 3D rendering of the object/patient based on the CT image using a virtual camera located at a position determined by the EM sensor fixed within the endoscope. If registration is correct, visualization of the anatomy may be substantially identical in the real and virtual images, although texture and colour may not be properly rendered in the virtual view. Other calibration methods may be used, as appropriate.

In this example, the coordinates of the EM sensor, and thus the endoscope camera coordinates, are registered to the coordinate system of the CT data set using fiducial markers placed on the exterior of the imaged subject. The fiducial markers are identified by an EM tracking tool and the locations in the EM coordinate system are registered to locations of the markers in the CT coordinate space. The position and orientation of the endoscope may now be tracked relative to the CT image and to the patient.

The set of 3D parametric data visualized in this example is radiation dose (e.g., planned or delivered). Radiation dose may be typically planned with respect to a CT image data set, typically the CT image data set used to register the set of 2D image data, as described above. However, if the radiation dose has been calculated or measured with respect to another set of 3D imaging data, the 3D radiation dose data may also be registered to the same CT imaging data as the 2D image data. This registration may be performed by, for example, identifying locations of common points within each data set, calculating the required coordinate system transformation matrix and applying the transformation to the coordinates of the set of 3D parametric data.

3D Surface Definition

A virtual 2D camera view, used to represent the actual view of the 2D camera at a given position and orientation, may be generated by first creating a viewing surface rendering of the CT image. In this example, the surface rendering includes a set of triangles and/or quadrilaterals assembled to create the viewing surface. Various appropriate techniques may be used for generating the rendered viewing surface. In this example, rendering of the viewing surface uses a CT # threshold value (e.g., a user-defined value) to define a boundary between air and tissue and thus the viewing surface to be rendered. The rendered surface may be viewed from any camera position and orientation. During the endoscopic procedure, the camera position and orientation data detected by the EM tracking sensors are used to define the virtual camera position and orientation for viewing the surface rendering of the CT image. This may result in the creation of similar or identical real and virtual endoscopic views. Using any suitable visualization software, for example, the real and virtual views may be displayed over top of each other with various appropriate transparency techniques used to vary the degree of visibility of either view, for example.

Determination of Parametric Contours

Various methods may be used to determine, from the set of 3D radiation dose data, the radiation isodose lines that lie on the tissue surface in the defined viewing surface. Some example methods are described below.

Intersection of Surfaces

This method calculates the intersection of two surfaces, namely the viewing surface, for example as defined in the manner described above, and an isodose surface calculated from the set of 3D radiation dose data, in this example. The calculated intersection is used to determine the isodose lines (which may also be referred to as contour lines or isolines) for visualization on the viewing surface. FIGS. 4A-4D illustrate an example of an example process of determining 3D contour levels that lie on the viewing surface.

Figure 4A:
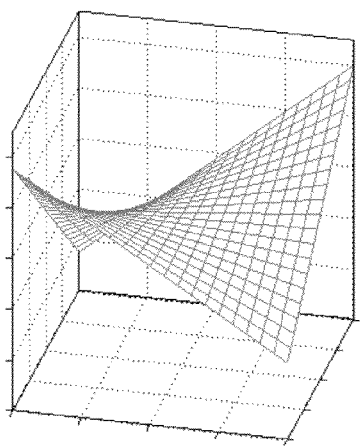
FIGS. 4A-4D schematically illustrate a process for registering 3D parametric data to a viewing surface.
Figure 4B:
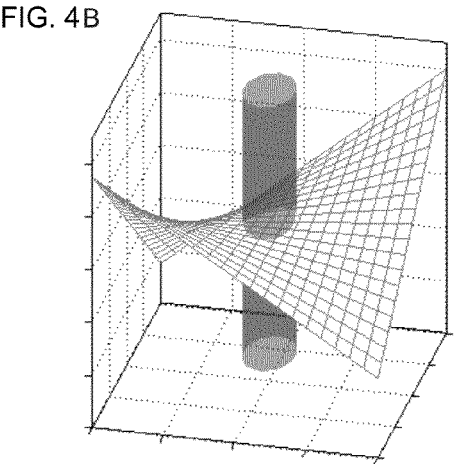
Figure 4C:
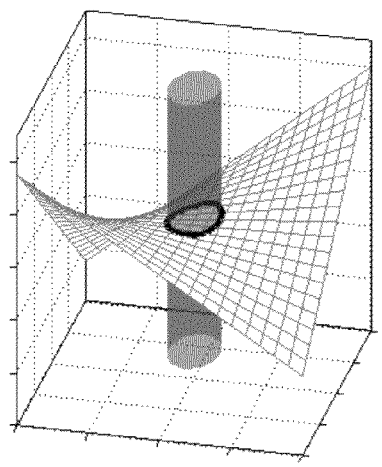
Figure 4D:
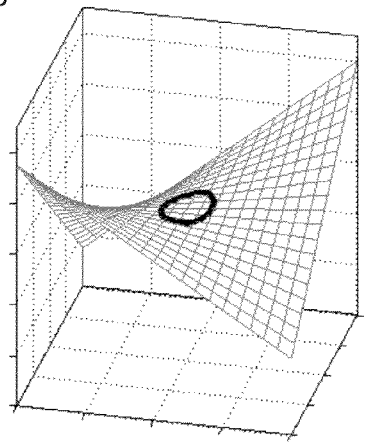

FIG. 4A shows an example of a defined viewing surface, for example based on a CT threshold value. The dose values or value ranges for visualization on this surface are first defined (e.g., via input by a user). Various appropriate methods may be used to find these desired isodose surfaces, for example using the same techniques used to generate the viewing surface rendering of the CT data set. FIG. 4B illustrates, in the form of a shaded area, an example isodose surface to be visualized on the viewing surface. The intersection of the isodose surface and the viewing surface may then be calculated. FIG. 4C illustrates the intersection of these surfaces in the form of a thick line on the viewing surface. As shown in FIG. 4D, the calculated intersection(s) may be represented as isodose line(s) visible on the viewing surface. This process may be repeated as necessary for any additional dose values or value ranges to be visualized.

In some examples, certain color(s) may be assigned to respective isoline(s), such that the value(s) represented by each isoline may be color coded. The set of isoline(s) (whether colored or not) may then be overlaid and/or underlaid on a 2D image, for visualization of the 3D parametric data (e.g., over a real-time 2D image).

Surface Constrained Contouring

Suitable contouring algorithms, for creating isoline(s) from the 3D parametric data, may operate on a regular 2D grid or 3D volume space. These algorithms may be appropriately modified so that searching is constrained to the viewing surface defined in the CT image data set. That is, creation of isoline(s) may be constrained such that only 3D parametric data corresponding to the viewing surface or the volume spanned by the viewing surface may be considered. This may help to avoid wasting processing power on calculations for data that are outside the volume of interest.

Surface Colour Mapping

Another example method for visualization of the 3D parametric data is described below. Again, this example is described in the context of viewing 3D radiation dose data.

This example method may create a copy of the rendered CT viewing surface described above that may be used as a color map to be overlaid and/or underlaid on the viewing surface. The coloring and transparency of the polygons defining this surface may be modified to identify those polygons that intersect with data points in the set of 3D parametric data having specified dose values or value ranges. This method may serve to not only identify the isodose lines, but also to visualize the dose values on a surface, using a color map.

Let G represent each polygon (e.g., each defined triangle or quadrilateral forming the surface) on the copied surface. Each polygon may have a color (c) and transparency (t) associated with it. The color and transparency of each polygon used to construct the surface may be adjusted as follows:

One or more isodose levels for visualization may be defined (e.g., by a user). A color may be assigned to each dose level, $D_{iso}$ for example, c=red for $D_{iso}$=100%, c=blue for $D_{iso}$=80%

Each polygon of the surface within the dose grid may be sampled.

If a given polygon is determined to overlap with a dose volume voxel having a dose value matching one of the one or more defined isodose levels to be visualized, the color used to define the polygon may be changed to match the assigned color for that dose, e.g., G(c)=red for $D_{iso}$=100%. The transparency may also set to opaque, e.g., G(t)=1. Where a given polygon is determined to be associated with two or more of the defined isodose levels, the polygon may be assigned color to match the highest associated dose level, or the lowest associate dose level, or an average of all associated dose levels, as appropriate. In some examples, the viewing surface may be recalculated to generate finer polygon partitions, for example based on the granularity of the set of 3D dose data, such that each polygon may at most be associated with one dose level.

If a given polygon is determined not to overlap with any of the defined isodose levels to be visualized, it may be made transparent, e.g., G(t)=0.

Visualization

From the set of 3D radiation dose data, isodose lines or a color map (e.g., as described above) corresponding to dose value(s) selected for visualization may be generated on the virtual rendered viewing surface. Hence, when an overlay and/or underlay view of both the real and virtual camera views is displayed, the radiation dose values (represented as isodose lines or a color map) may be displayed on top of the real-time 2D camera view. As the endoscope moves through the patient, and the 2D image correspondingly updates in real-time, the overlay and/or underlay of the 3D dose data may remain consistent with the 2D image being viewed.

IsoDose Line Visualization

The isodose lines, for example calculated using one of the methods described above, may be displayed in a 2D image in various ways. Some examples are described below.

As described above, the isodose lines may be overlaid and/or underlaid on the virtual viewing surface. A virtual 2D image may be generated by using a virtual camera at any point in 3D space. This may be done using any appropriate imaging software. If part of the viewing surface is hidden (e.g., overlapped) in the virtual 2D image, any isodose lines corresponding to the hidden part of the surface may also be hidden when visualized in the 2D image.

Visualization of the isodose lines on the real 2D image may be performed by overlay and/or underlay of the virtual 2D image over the real 2D image and adjusting the transparency of the virtual 2D image appropriately so that the real 2D image is visible, but overlaid and/or underlaid with the isodose lines. This process may be aided by coloring the surface of the virtual 2D image so as to generally match the coloring of the real surface being imaged. An example of this visualization method is shown in FIG. 1.

FIG. 1 shows an example screen shot showing radiation isodose lines displayed over a real 2D endoscopic image. In this example, the upper images show axial, coronal and sagittal views of a skull-shaped phantom. The white lines in these figures show the position and orientation of an endoscopic camera. The bottom left image shows the real endoscopic 2D image. The bottom right image shows an overlay and/or underlay of the endoscope 2D image with the radiation dose lines on the tissue surface, along with a scale bar indicating the dose values represented by different colors of the dose lines.

In some examples, such as where the color of the real surface is not essentially a single color, a method different from that described above may be used. For example, adjusting the transparency levels of the isodose overlay and/or underlay, so that the real 2D image is visible may also reduce visibility of the isodose lines. Reducing the transparency of the real 2D image so that the isodose lines are visible may reduce visibility of the real surface and may reduce the impact of observing the dose lines on the real image. Removing the virtual surface and keeping the isodose lines visible may result in a situation where segments of the isodose lines that would otherwise be hidden by tissue (i.e., they are behind overlapping tissues) are still visible.

Figure 5:
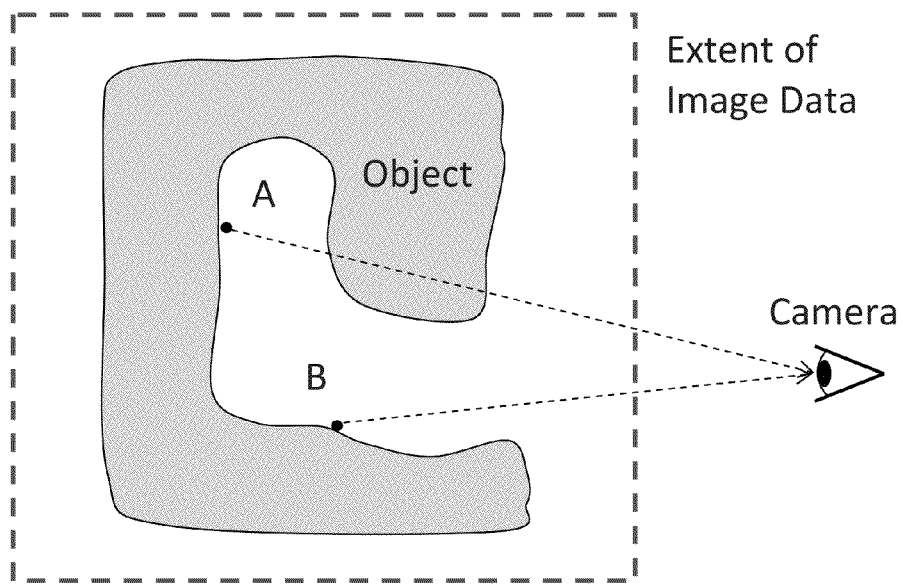
FIG. 5 is a schematic diagram illustrating how a 3D viewing surface may be matched to a 2D view.

FIG. 5 illustrates an example method for limiting which isodose lines should be visible in such a case. This example method may define which isodose segments or points should be visible (i.e., not hidden by overlapping tissues) in the real 2D image.

This method may begin by storing or receiving the CT # threshold value that was used to define the viewing surface of the tissue, T. Then, for each isodose point (e.g., point A or point B) on the surface, a vector is calculated from the point to the position of the virtual camera. Starting from the isodose point (e.g., A or B), the following determination is made for each point defined in small increments along the vector: for each incremental point along the vector, a determination is made whether the incremental point is associated with a CT# value that is greater than $T_S$ (i.e., CT#>$T_S$)—if so, then that point is within or overlapped by the viewing surface from the viewpoint of the camera and the isodose point (e.g., A) associated with that vector should be hidden from view and the determination is done; if not, then the next incremental point is evaluated, until either CT#>$T_S$ is found or the camera position is reached or the incremental point is outside the range of the image, indicating that the isodose point (e.g., B) associated with that vector should be visible.

Once the above determination is made for all isodose points, only those determined to be visible are displayed. This process may be repeated each time the camera position and/or orientation changes.

Color Map Display

In some examples, in addition to or alternative to displaying the set of 3D parametric data (such as radiation dose data) as isolines, the set of 3D parametric data may be displayed as a color map of the viewing surface, overlaid and/or underlaid onto the real 2D image.

Figure 2:
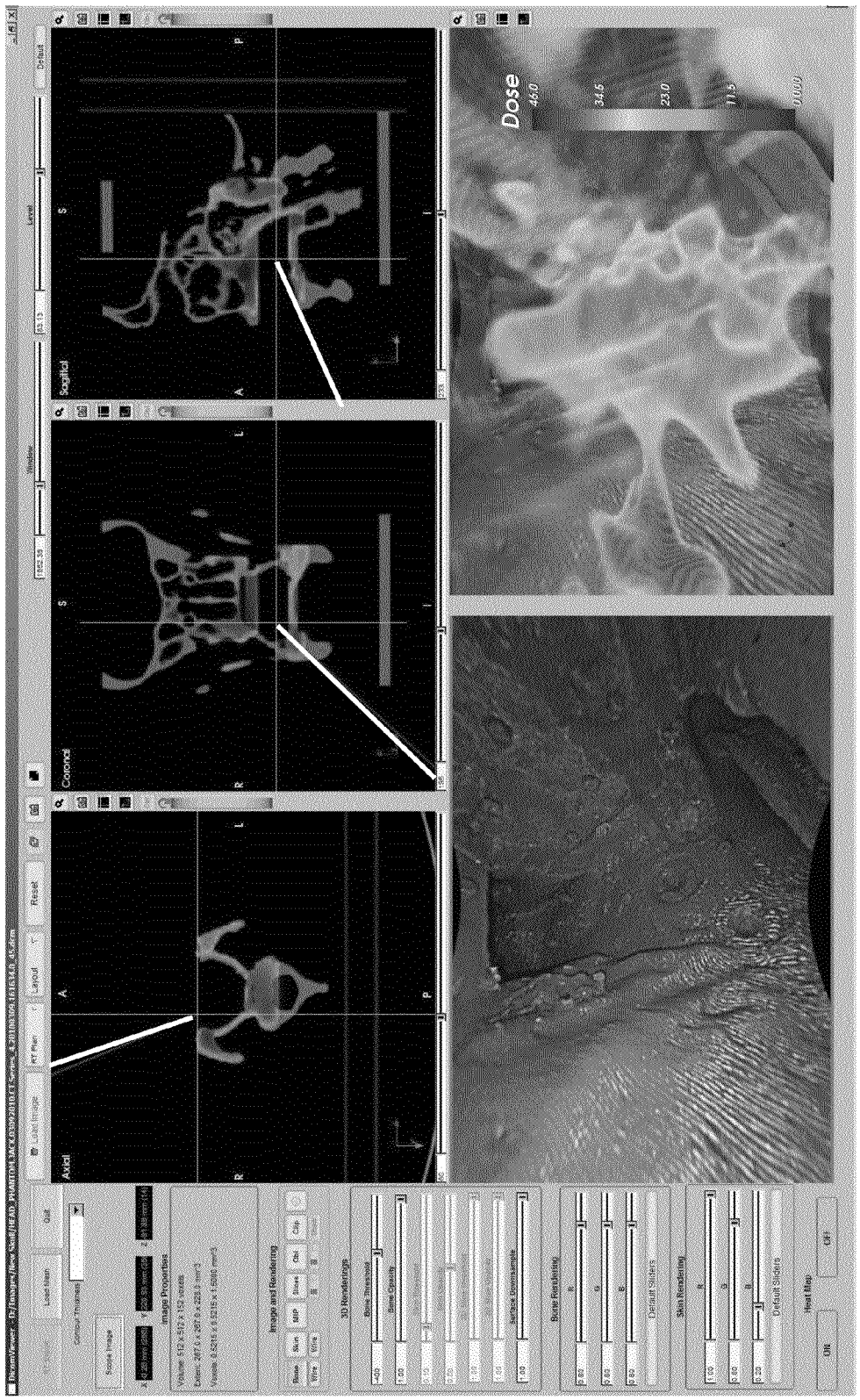
FIG. 2 shows a screen shot illustrating another example implementation of the disclosed methods and systems, using a color map.

This may be carried out using volume rendering of the 3D parametric space rather than creating isosurfaces or contours. An example of this process is described below. The bottom right image in FIG. 2 shows an example image generated using an example of this method.

Background or null data may be defined to be colorless or transparent in the color map. In the example of 3D radiation dose data, "air dose" data may be set it to a color or transparency value of 0, based on a mask defined using the CT value of the image. An "air dose" may refer to a radiation dose calculated in low density regions such as air gaps in the nasal cavity, bronchus, esophagus or lungs, which may be considered background dose levels. Typically, only the dose at the surface of the tissue visible in the real 2D image needs to be visualized.

A mask may be calculated using the CT # threshold value (e.g., defined by a user) used to define the boundary between air and tissue for the generation of the viewing surface, as described above. If voxel in the 3D parametric data set (in this case dose data) is in the same 3D space as a voxel of the CT data set below the CT threshold value (i.e., is not part of the viewing surface), the parametric value of that voxel in the 3D parametric data set is set to zero.

Once the mask has been defined, the remaining non-zero voxels in the 3D parametric data set should be those associated with the viewing surface.

The parametric values or value ranges to be visualized may be determined, for example based on user input or a pre-set default level. The value ranges to be visualized may be defined by a minimum and a maximum value. Based on the values or value ranges to be visualized, a color scale may be defined, such that each value maps to a unique color. This means that, for a set of 3D radiation dose data, all voxels having the same dose level or within the same range of dose levels would be visualized in the same color. In some examples, the color scale may be continuous, such that a continuum of dose values may be visualized. In other examples, the color scale may be discrete, such that a sub-range of dose values is grouped together for each color.

Each voxel may be then associated with the appropriate color, based on its parameter value, in order to general a color map.

Those voxels having parameter values below the minimum value may be made transparent. Those voxels with parameter values higher than the minimum may be made opaque. Since the mask calculated previously may set values of zero for all voxels that are not part of the viewing surface, the effect of this may be to only make visible those voxels visible by the 2D camera.

The generated color map may be then overlaid and/or underlaid over the real 2D image. An example is shown in the screenshot of FIG. 2. In FIG. 2, the upper images may be similar to those of FIG. 1, with the camera view being indicated by white lines. The bottom left image shows the real 2D image. The bottom right image shows the 2D image overlaid with a color map of dose levels, along with a color scale indicating the dose values associated with each color.

Although FIGS. 1 and 2 show examples of visualization in which the user is also presented with an image of the virtual surface, in some examples the virtual surface may not be displayed. For example, FIG. 8 (described further below) shows an example of visualization in which the top two and bottom left images indicate the orthogonal view, and the bottom right image shows the 3D dose data, in the form of isolines in this example, overlaid on the actual 2D image.

Example 2

In the example described below, a method for displaying the dose levels using a transparency mask is described. This method may be useful where the color of the real surface may not be essentially a single color. In example color displays where a transparency mask is not used, the color of the rendered surface viewed in the virtual image may be set to closely match that of the actual tissue observed in the real image. Where a transparency mask is used, the color of the surface rendering may be set to black, leaving only the colored isolines visible within the render window. The black surface rendering may be used to identify only those segments of the surface dose that are visible to the camera. As the virtual camera position changes, new surface segments may be exposed and others may be hidden, along with any dose information displayed on the segment.

Frames from the virtual 2D image may be captured and a transparency channel (e.g., an alpha channel) may be appended to each RGB frame, which may set the black pixels to be rendered as transparent. The RGB frame may be first converted to grayscale through a magnitude filter. The grayscale image may be passed through a threshold filter to produce an alpha channel where each pixel may be either transparent or opaque. The alpha channel may be then appended to the RGB frame to produce the RGBA frame. The output RGBA frame may be registered to the real image window (e.g., as a separate layer overtop of the real video layer). Through this process, only those pixels in the virtual 2D image that are not black may be visible on the real image.

The methods and systems used in this example may be similar to those described above in Example 1.

Radiation Dose Display

The display calculations and process may be as described above with reference to FIGS. 3A and 3B. The display of the real video may be defined as the real window and that of the virtual endoscopic view may be defined as the render window. Within each window, layers of information may be displayed at varying levels of transparency. Display of the radiation dose onto the endoscopic image may include selective registered overlay and/or underlay of information generated in the render window onto the real window. In the present example, the real window may be displayed with at least two layers of information: the underlying video layer and the overlying dose layer.

The dose display algorithm may be as described above with reference to FIGS. 3A and 3B. In the render window, two layers of data may be displayed. The first layer may be a viewing surface of the CT image generated using a standard air/tissue threshold value (e.g., about −500 HU). The color of the viewing surface may be set to match a pre-defined transparency mask color. For example, the mask color may be black since black typically does not match any of the colors used in colormapping of the radiation dose values, however any suitable mask color may be used. For example, the mask color may be any color that does not overlap with the colors used in the colormap and/or defined in the colorscale. The second layer may contain dose information. In this example, the DICOM RT dose file may be read using the DICOM Toolkit (DCMTK).

The dose data may be represented as volumetric data in CT space as dose voxels, where the dose value at Cartesian coordinates k may be defined as $I^{dose}(k)$. Only dose on the surface rendering may be displayed. Let $V^{dose}$ denote the set of points contained by the dose volume in CT space, P the set of points of the surface rendering, and $k_{P_i}$ the Cartesian coordinates of the $i^{th}$ surface point. Every surface point $p_i$ in P may be assigned a scalar value $f_{P_i}$, where $$f_{P_i} = \begin{cases} I^{dose}(k_{P_i}), & k_{P_i} \subset V^{dose} \\ 0, & k_{P_i} \not\subset V^{dose} \end{cases} \quad (1)$$

In the above description, the scalar assigned to each surface point may represent the dose at the same coordinates as the surface point. In cases where dose buildup occurs at the surface, such as with megavoltage beams, it may be more useful to display dose values below the surface. In these cases, the coordinates for the dose may be chosen at a user-defined depth, d, which may be along the normal, n, from each surface point below the surface.

$$f_{P_i} = \begin{cases} I^{dose}(k_{P_i} - n*d), & k_{P_i} \subset V^{dose} \\ 0, & k_{P_i} \not\subset V^{dose} \end{cases} \quad (2)$$

The density of surface points may be greater than the dose grid and so the display of the dose on the surface may be limited by the resolution of the dose grid. For visualization, this may lead to sharp dose boundaries on the surface. To generate smoother dose visualization, the scalars of the surface points may be smoothed using a weighted average. For example, a KD-tree may be used to locate neighbouring surface points within a maximum distance $d_{max}$ of, for example, 5 mm to a query surface point. For a surface point $p_i$ let J denote the set of its neighbouring points determined from the KD-tree. Each neighbour point is assigned a weight $w_{ji}$, where $$w_{ji} = 1 - \frac{\|k_{P_j} - k_{P_i}\|}{d_{max}}, \quad \|k_{P_j} - k_{P_i}\| < d_{max} \quad (3)$$

$$w_{ji} = 0, \quad \|k_{P_j} - k_{P_i}\| \geq d_{max}$$

The average scalar $f_{P_i}^{average}$ may be then calculated as $$f_{P_i}^{average} = \frac{f_{P_i} + \sum_j w_{ji} f_{P_j}}{1 + \sum_J w_{ji}} \quad (4)$$

Once scalar values for the surface points are calculated, dose visualization may be displayed as either a colorwash and/or as isodose lines. Radiation dose values may be assigned to colormap values (e.g., C(r,g,b)=fn(Dose)). The user may be provided with options for setting window and/or level values for the colormap. In some examples, the level values may be preset to a default value and/or may not be adjustable by the user. Radiation doses below the set level may be displayed as black, which may results in the below-level doses being transparent (and therefore not visualized) on the video display. In some examples, for the colorwash visualization, surface normals may be also calculated to interpolate rendered pixel values using Phong shading.[11]

For a colorwash display, the individual isosurface shapes may be assigned a color from the colormap based on the value of $f_{P_i}^{average}$. For display of isodose lines, isolines may be generated using 3D marching cubes[12] over the set of $f_{P_i}^{average}$, with bands and edges extracted. Single colors may be assigned to individual isodose lines based on the colormapping.

As noted earlier, the color of the surface rendering may be set to black, leaving only the colored isolines visible within the render window. The black surface rendering may serve to identify only those segments of the surface dose that are visible to the camera. As virtual camera position changes, new surface segments may be exposed and others hidden, along with any dose information displayed on the segment.

Frames from the render window may be captured and a transparency channel (e.g., an alpha channel) may be appended to each RGB frame, setting the black pixels transparent. The RGB frame may be first converted to grayscale through a magnitude filter. The grayscale image may be passed through a threshold filter to produce an alpha channel where each pixel may be either transparent or opaque. The alpha channel may be then appended to the RGB frame to produce the RGBA frame. The output RGBA frame may be added to the real window as a separate dose layer (e.g., overlay or underlay) of the video layer. For the colorwash display, a second transparency level for the whole layer may be used to enable adjustment of the overall transparency of the dose display level with respect to the endoscopic image.

Calculation of the isodose lines and colorwash values may only occur once (e.g., immediately or shortly after loading of the radiation dose data). The transparency of dose segments may be updated with each camera view. FIG. 9 lists examples of frame rates using data from three example head and neck cancer patients and two phantom data sets. The frame rates for the isoline and colorwash case are compared to the baseline images with no dose display. Using an Intel i7-920 2.67 GHz processor with 6 GB of RAM, the average frame rate was found to be about 7.64 frames per second without dose visualization, 3.94 with isodose lines overlaid on video, and 2.03 with dose colorwash overlaid on video. It may be that the majority of the processing time occurs when capturing the render window, which may scale linearly with the number of polygons to render. For the patient renderings, the average processing time to capture one frame in the render window was found to be about 244 ms. To accelerate the visualization, the captured isolines or colorwash frames may be stored in memory. The size of the frames may be reduced, for example by a factor of 3, to reduce memory load with acceptable dose resolution on video/images Comparison of Visualization Accuracy Accuracy of the dose visualization created in this example was tested by creating a radiation treatment plan for a simple cylindrical phantom with markings at known positions and comparing the actual isodose line positions with the marking positions. The cylindrical plastic phantom used in this example comparison had a hollow interior with 1 cm grid extending out from the interior by 1 mm. Following CT simulation of the phantom, a radiation plan was created (Pinnacle V.9, Philips) so that isodose lines at 20, 25, and 30 Gy matched radial interior markings separated by 2 cm.

For isodose visualization during endoscopy, the CT image and radiation dose grid of the phantom were imported into the visualization/registration software using standard Dicom protocols. Registration of the tracking and CT image coordinate systems in this example was performed by identifying known fiducial points on the exterior of the phantom using a tracked pointing tool. Endoscopic video was captured of the interior of the phantom with the isodose lines visible during recording. After data collection, the video was reviewed and several representative images were captured at points within the phantom (see FIGS. 6A-6E).

The interior grid of the phantom was defined along the axial and longitudinal grid lines: the axial lines form circles on the interior of the phantom, while the longitudinal lines extend along the length from the base of the phantom to its opening. Visually, the isodose lines was found to closely match the axial grid lines. Where they intersect the longitudinal grid lines, a small projection towards the center of the phantom was observed. These projections and their corresponding points on the phantom were identified for each axial isodose and grid line. Twelve such markings were identified. The distance between isodose and grid points was measured and the root mean square error between them calculated. This process was repeated three times for each isodose line.

FIGS. 6A-6E shows examples of visualization of dosage in phantom tests of isodose display, using an example of the disclosed methods and systems. FIG. 6A shows an example treatment plan in Pinnacle showing (top) isodose lines in sagittal view and (bottom) colorwash on clipped 3D rendering. FIG. 6B shows an example endoscopic view overlaid with 20, 25 and 30 Gy isodose lines. FIG. 6C is similar to FIG. 6B but showing an example colorwash overlaid on the endoscopic view. FIG. 6D shows another example endoscopic view overlaid with 25 and 30 Gy isodose lines. FIG. 6E is similar to FIG. 6D but showing an example colorwash overlaid on the endoscopic view.

FIGS. 6A-6E shows several example images of the isodose display on the hollow phantom. Based on the treatment plan, isodose lines at 20, 25 and 30 Gy are designed to coincide with the axial gridlines at 2 cm intervals. Close examination of the final plan showed that the isodose lines match the grid positions to less than 1 mm variation. The axial slice thickness of 0.625 mm may represent a lower limit on the accuracy of the correspondence between isodose line and grid marking in this example. FIG. 6A shows the location of isodose lines using the treatment planning software for both a coronal view of the phantom (top) and a surface rendering with colorwash (bottom). These images show the congruence of the 20, 25 and 30 Gy isodose lines with the internal grid markings.

In FIG. 6B, the locations of the 20 and 25 Gy isodose lines are evident; while in FIG. 6D the 25 and 30 Gy isodose lines are evident for comparison to their respective gridline positions. In FIG. 6B, the respective errors in isodose positions between the grid markings and the corresponding isodose positions for 20 and 25 Gy lines were found to be 1.31±.05 and 1.55±.02 mm while in FIG. 6D, the errors for the 25 and 30 Gy lines were found to be 0.64±0.03 and 0.53±0.10 mm. The results were found to be within the error of the axial resolution and registration error between the endoscopy and CT image sets.

Clinical Usage

To demonstrate the isodose display in a more relevant situation, an example of clinical usage was studied. A male patient with T1a N0 M0 laryngeal cancer was examined within an institutionally approved clinical trial protocol using the tracked endoscopic system. A CT image of the patient was first acquired for purposes of treatment planning. The patient was imaged with an immobilization mask (e.g., an S-frame) in place. The patient was subsequently examined in the same position again with the immobilization mask in place using the endoscopic tracking system. Endoscopic video and tracking coordinates were simultaneously recorded for later review. Registration between the endoscopy and CT images were corrected retrospectively using anatomical landmarks visible in both real and virtual images.

Figures 7A, 7B, 7C, 7D, 7E:
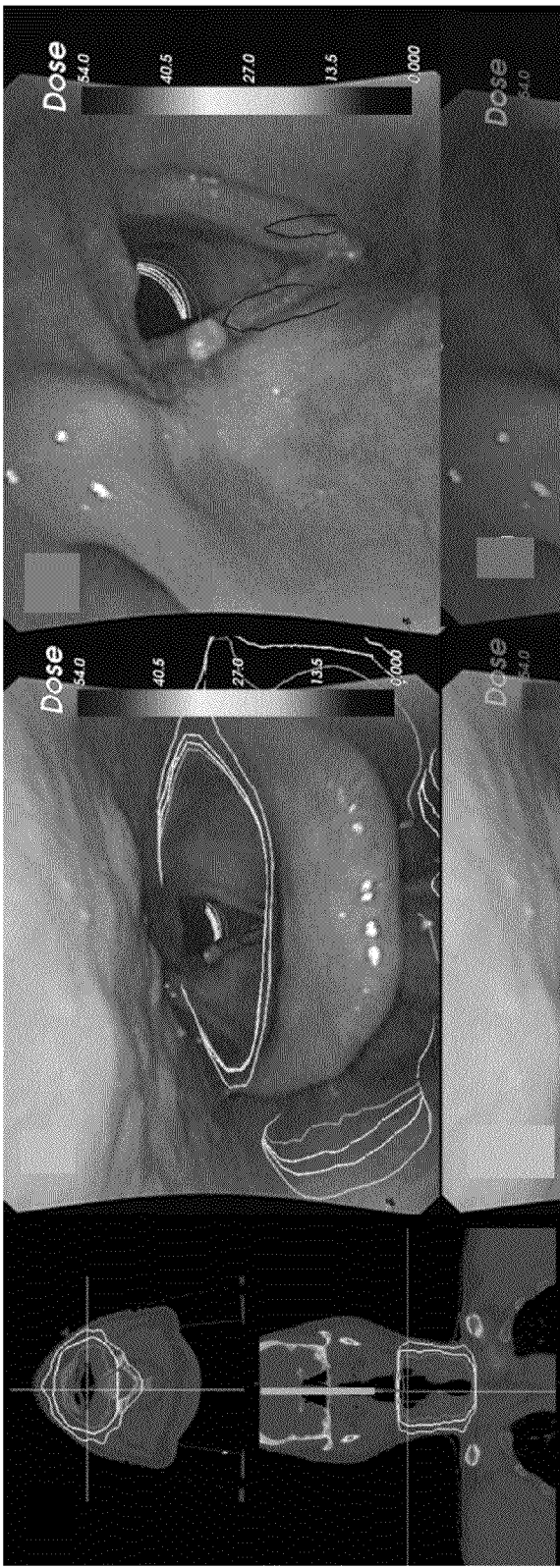
FIGS. 7A-7E shows examples of clinical usage of an example of the disclosed methods and systems for radiation dose visualization.

A clinical example of the radiation dose display is presented in FIGS. 7A-7E. FIGS. 7A-7E shows examples of clinical usage of an example of the disclosed methods and systems for radiation dose display. FIG. 7A shows an example treatment plan in Pinnacle showing isodose lines along three orthogonal planes. Endoscope positions for subsequent images are shown as lines. Examples of isodose lines (FIG. 7B) and colorwash (FIG. 7C) renderings are displayed overlaid on an example endoscope image obtained from a first position, just superior to glottis and extent of radiation dose. Examples of isodose lines (FIG. 7D) and colorwash (FIG. 7E) renderings are displayed overlaid on example endoscope image obtained from a second position. The tumor is visible on the epi-glottis.

In FIGS. 7A-7E, examples of both isodose and colorwash displays are shown. In the colorwash images, the lowest displayed dose in this example is 6Gy and the transparency of the colorwash in this example is set at 0.5. The endoscopic images are captured from two positions. FIGS. 7B and 7D are taken in a position superior to the lowest isodose line. The rapid fall-off in dose along the tissue surface is visible here, including the dose lines on the posterior side of the glottis. The colorwash image shows the low dose delivered to the glottis and the extent of the high dose region surrounding the larynx. Deeper into the trachea, the high dose region proximal to the tumour region is visible. FIGS. 7C and 7E are taken closer to the location of the tumor, which is visible as a small nodule on the epi-glottis. The isodose lines show only the highest dose level immediately superior to the epi-glottis, while the colorwash image shows the entire region surrounding the larynx covered in high dose radiation.

There may be limited registration accuracy between the endoscopy and CT image sets (which may nonetheless be clinically negligible and/or acceptable). For example, a slight error in registration may be observed in FIG. 7C, where the blue colorwash (indicated by white arrow) over the glottis is slightly larger than the real glottis. This slightly expanded dose region may be due to either a small registration error or in the setting of the CT threshold value in generating the virtual surface. Using a low value may generate a virtual surface that is slightly expanded from the actual visible surface. In either case, the error is less than 2 mm, which may be clinically negligible and/or acceptable. This error may be reduced or eliminated through selection of the values for defining the virtual surface, or by other methods.

Figure 8:
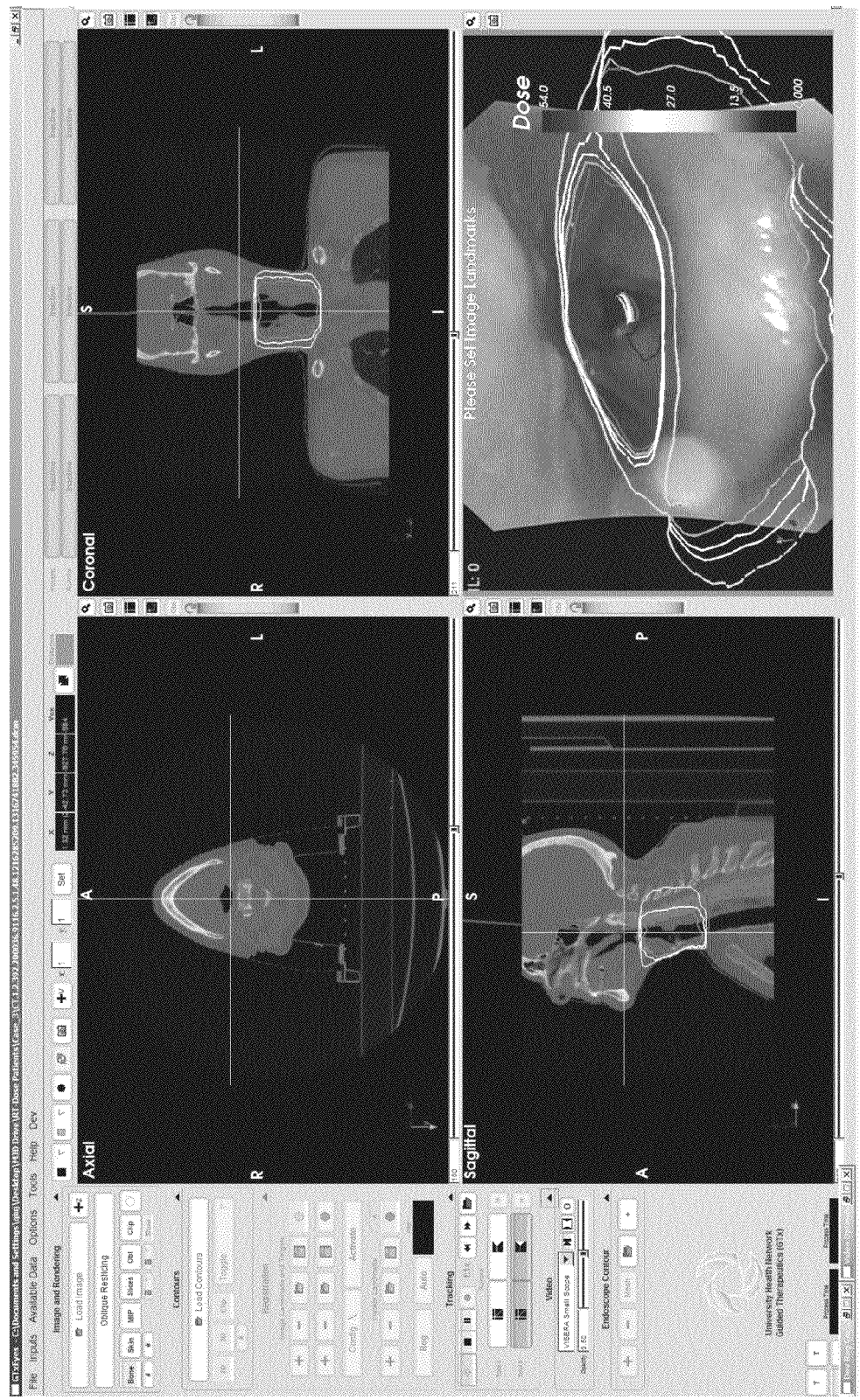
FIG. 8 shows another example of the disclosed methods and systems for use in radiation dose visualization.

FIG. 8 shows another example of a visualization display, at camera positions similar to those of FIGS. 7A-7E. In FIG. 8, only isodose lines are visualized, overlaid on the 2D endoscopic image (bottom right view). The other three views may be used to indicate the camera position of the overlaid view. The user may be provided with options for selecting what views to be displayed (e.g., views indicating camera position, view of virtual viewing surface, view of 2D image without parametric data, and/or view of 2D image with registered parametric data).

User selectable options for controlling the display may be provided in a toolbar (in this example, in a panel on the left side). Options for controlling the display may include, for example, one or more of: selection of 2D image data to view; selection of 3D parametric data to view; selection of tissue to view (e.g., bone or skin); selection of whether to view isolines or colormaps or both; selection of 2D or 3D rendering of parametric data; selection of points and/or portions of viewing surface for which to display rendered and/or actual parametric values; selection of registration landmarks to view; options for controlling video display of 2D image data; selection of threshold for parametric values to display; selection of colorscale; selection of color or grayscale view; and other suitable image viewing options that may be provided in an imaging workstation, for example.

Discussion

The above examples illustrate the ability to display 3D parameters on a video image of a non-planar surface. The above examples illustrate that planned radiation dose may be displayed on endoscopic images using an example of the disclosed methods and systems. In phantom tests, an accuracy of 0.6-1.5 mm was found, which may be within the accuracy of the tracking tools and image resolution. Registration error between the video and 3D images sets may be a source of visualization error. The frame rate of visualization in these examples may be about ⅓ that of the standard video. This frame rate may be improved with improved computing power, for example. In these examples, the endoscopy is registered to the planning CT and thus to the dose grid. Consequently, it may be necessary for the patient to be positioned as they were in the CT-simulator. In some examples, methods of deformable registration may be used to account for variations in patient anatomy following treatment and patient position during the endoscopy procedure, such that the patient may not be necessarily positioned as in the CT-simulator.

The display of radiation dose on endoscopic images may, in radiation therapy, serve to provide quantitative measures with respect to delivered dose when assessing tissue response. Directly relating tumor response as observed endoscopically to the spatially resolved dose distribution may be useful in adaptive radiation therapy for many endoluminal cancers. The dose display may also be useful for quantitative assessments of toxicities with delivered surface dose for many clinical complications in luminal organs such as radiation proctitis, mucasitis and esophagitis, among others. Relating clinical grading of such conditions directly to the dose rather than volumetric measures may help to improve the clinical care of individual patients and improve understanding of how these conditions arise. Relating dose to a visual display may also be useful for patients first treated with radiation therapy, followed by surgery. In these cases, visualization of the dose may aid the surgeon in defining resection margins.

The registration and display of radiation dose with endoscopic imaging has a possible role in adaptive radiotherapy,[14,15] for example in assessing treatment response between fractions during the course of treatment. Endoscopic examination of head and neck patients typically occurs several times following treatment for assessment of tumor regression and normal tissue. Analogous to the proposed role of PET or MRI imaging,[16-19] endoscopy may also be used to assess tumor response and toxicities and could enable some measure of dose painting, by reducing dose to normal tissues if early signs of acute toxicities are observed or increasing dose if tumor regression is not evident. The present disclosure may provide a method for direct spatial correlation of the endoscopic findings to the radiation dose.

Assessing tissue response with respect to radiation dose may be useful in understanding normal tissue complication probabilities (NTCP), and hence in calculating optimal therapeutic ratios. Emami[4] defined tolerance doses for irradiation of partial or whole volumes of various organs, using consensus of clinical experience to define NTCP levels. Recognizing the limitations of this approach and increased dose modulation with modern RT techniques, the QUANTEC initiative[5] attempts to derive quantitative correlation between dose received and normal tissue response. Various normal-tissue response studies reviewed and highlighted by QUANTEC relate NTCP to volume measures of dose, such as mean dose to target or tissue, or DVH parameters. This methodology may be suitable for clinical conditions arising from toxicities for whole organs; consider for example parotid dose constraints and salivary production.

Normal tissue toxicities arising from damage to superficial surfaces of luminal organs, such as radiation proctitis, mucasistis and esophagitis, may be evaluated using endoscopy. With no direct spatial correlation between the observed tissue effects, and the dose delivered, often assessment of these toxicities may relate general clinical outcomes to dose volume or Dose Surface Histogram measures.[13-16] Dose Surface Histograms have been developed for assessing rectal toxicities following prostate irradiation, but rather than compare dose to specific sites of rectal tissue damage, DSH measures may be typically compared to general clinical toxicity gradings (e.g., Grade 2—symptoms responding to simple outpatient management).[17,18] This methodology may be understandable clinically for rectal toxicities following irradiation of the prostate, where excessive probing of the organ may contribute to further clinical damage. However, this methodology may not enable differentiation of mottled damage in the rectum versus damage to one large area. This methodology may be also used in assessment of acute esophagitis due to treatment of non-small cell lung cancer, where a large variety of dose parameters have been correlated to clinical scoring of acute esophagitis (see [19] for a review of these studies). Correlating dose and toxicity may be confounded by variations in grading the clinical effect (e.g., due to physician variation in the clinical scoring and underlying or pre-existing conditions) and the large range in metrics used to quantify esophageal dose. A more direct measure of the toxicities associated with radiation therapy may be found in several studies[20,21] correlating acute edema in the larynx (e.g., observed using flexible endoscopes) to dose following treatment of head and neck cancers. DVH parameters were compared to edema scores, finding V50 correlated strongly to Grade 2+ edema. Such edema scoring seems an improvement in assessing toxicity when compared to clinical grading. However, it still may not present a direction correlation of dose to edema in the same location.

The combination of radiation therapy and surgery may be used in various cancer sites, for example using radiation post-surgery to ensure complete treatment of margin resections, or radiation pre-surgery for debulking of the primary tumor site. In lower limb sarcomas, radiation may be used prior to surgery to reduce the volume of the tumor. Conventional treatment planning process typically starts with the surgeon delineating the area of skin and subcutaneous tissues that would later comprise the surgical flaps in the 3D RT planning system[28]. This may serve as an organ at risk for dose avoidance in IMRT optimization. These virtual flaps may not exist until the time of surgery and may be based on the principles of sarcoma surgery for each individual patient. Prior to surgery, the IMRT dose distribution may be mapped on the surface of the patient's skin using an optical localization system to guide the placement of incisions to the lower dose skin region. To help avoid this process of manual tracking and to help decrease the procedure time, the dose distribution may be visualized overlaid/underlaid real-time video of the tissue surface, using an example of the disclosed methods and systems. The surgeon may then follow any dose line for incision.

With the direct registered overlay/underlay of dose on the endoscopic imaging presented in the present examples, using an example of the disclosed methods and systems, tissue toxicities and tumor response in endoluminal organs may be directly correlated to the actual tissue dose, offering the capacity for adaptive radiation therapy in these organs, and a more nuanced assessment of normal tissue toxicities following radiation therapy.

The embodiments of the present disclosure described above are intended to be examples only. Alterations, modifications and variations to the disclosure may be made without departing from the intended scope of the present disclosure. In particular, selected features from one or more of the above-described embodiments may be combined to create alternative embodiments not explicitly described. All values and sub-ranges within disclosed ranges are also disclosed. The subject matter described herein intends to cover and embrace all suitable changes in technology. All references mentioned are hereby incorporated by reference in their entirety.

REFERENCES

1. M. Caversaccio, J. G. Giraldez, R. Thoranaghatte, G. Zheng, P. Eggli, L. P. Nolte, and M. A. G. Ballester, Rhinology 46, 156-158 (2008).
2. M. P. Fried, S. R. Parikh, and B. Sadoughi, Laryngoscope 118, 1287-1292 (2008).
3. W. E. Higgins, J. P. Helferty, K. K. Lu, S. A. Merritt, L. Rai, and K. C. Yu, Computerized Medical Imaging and Graphics 32, 159-173 (2008).
4. B. Emami, J. Lyman, A. Brown, L. Coia, M. Goitein, J. E. Munzenrider, B. Shank, L. J. Solin, and M. Wesson, International Journal of Radiation Oncology Biology Physics 21, 109-122 (1991).
5. S. M. Bentzen, L. S. Constine, J. O. Deasy, A. Eisbruch, A. Jackson, L. B. Marks, R. K. Ten Haken, and E. D. Yorke, International Journal of Radiation Oncology Biology Physics 76, S3-S9 (2010).
6. N. C. Atuegwu and R. L. Galloway, Physics in Medicine and Biology 53, 4355-4368 (2008).
7. J. Hummel, W. Birkfellner, T. Figl, C. Haider, R. Hanel, and H. Bergmann, Medical Imaging 2002: Visualization, Image-Guided Procedures, and Display 4681, 94-99 (2002).
8. P. Reittner, M. Tillich, W. Luxenberger, R. Weinke, K. Preidler, W. Kole, H. Stammberger, and D. Szolar, European Radiology 12, 592-596 (2002).
9. A. Khoury, J. H. Siewerdsen, C. M. Whyne, M. J. Daly, H. J. Kreder, D. J. Moseley, and D. A. Jaffray, Computer Aided Surgery 12, 195-207 (2007).
10. M. Daly, J. Siewerdsen, D. Moseley, Y. Cho, S. Ansell, G. Wilson, and D. Jaffray, Medical Physics 34, 2635-2635 (2007).
11. B. T. Phong, Communications of the Acm 18, 311-317 (1975).
12. W. E. Lorensen and C. H. E., Computer Graphics 21, 163-169 (1987).
13. S. M. Zhou, L. B. Marks, G. S. Tracton, G. S. Sibley, K. L. Light, P. D. Maguire, and M. S. Anscher, Medical Physics 27, 1727-1731 (2000).
14. G. J. Meijer, M. Van den Brink, M. S. Hoogeman, J. Meinders, and J. V. Lebesque, International Journal of Radiation Oncology Biology Physics 45, 1073-1080 (1999).
15. P. D. Maguire, G. S. Sibley, S. M. Zhou, T. A. Jamieson, K. L. Light, P. A. Antoine, J. E. Herndon, M. S. Anscher, and L. B. Marks, International Journal of Radiation Oncology Biology Physics 45, 97-103 (1999).
16. S. D. Li, A. Boyer, Y. Lu, and G. T. Y. Chen, Medical Physics 24, 1107-1116 (1997).
17. Y. Lu, S. Li, D. Spelbring, P. Song, S. Vijayakumar, C. Pelizzari, and G. T. Y. Chen, Medical Physics 22, 279-284 (1995).
18. R. Munbodh, A. Jackson, J. Bauer, C. R. Schmidtlein, and M. J. Zelefsky, Medical Physics 35, 2137-2150 (2008).
19. M. Werner-Wasik, E. Yorke, J. Deasy, J. Nam, and L. B. Marks, International Journal of Radiation Oncology Biology Physics 76, S86-S93 (2010).
20. T. Rancati, M. Schwarz, A. M. Allen, F. Feng, A. Popovtzer, B. Mittal, and A. Eisbruch, International Journal of Radiation Oncology Biology Physics 76, S64-S69 (2010).
21. T. Rancati, C. Fiorino, and G. Sanguineti, International Journal of Radiation Oncology Biology Physics 75, 915-923 (2009).
22. T. Pavlidis "The Use of a Syntactic Shape Analyzer for Contour Matching," *IEEE Trans. Pattern Analysis and Machine Intelligence*, PAMI-1 (1979), pp. 307-310.
23. T. Pavlidis, "Algorithms for Shape Analysis of Contours and Waveforms," *IEEE Trans. Pattern Analysis and Machine Intelligence*, PAMI-2 (1980), pp. 301-312.
24. P. Bourke, "CONREC: A Contouring Subroutine", Byte Magazine, 1987.
25. http://www.imageprocessingplace.com/downloads_V3/root_downloads/tutorials/contour_tracing_Abeer_George_Ghuneim/index.html
26. W. E. Lorensen, H. E. Cline: *Marching Cubes: A high resolution 3D surface construction algorithm*. In: Computer Graphics, Vol. 21, Nr. 4, July 1987.
27. T. Y. Lee, C. H. Lin, Growing-cube isosurface extraction algorithm for medical volume data, Comput Med Imaging Graph. 2001 September-October; 25(5):405-15.
28. C. I. Dickie; A. Griffin; A. Parent; P. Chung; C. Catton; J. Wunder; P. Ferguson; M. Sharpe; R. Bell; B. O'Sullivan, "Phase II Study of Preoperative Intensity Modulated Radiation Therapy for Lower Limb Soft Tissue Sarcoma", International Journal of Radiation Oncology, Biology, Physics (November 2010), 78 (3), Supplement, pg. S84-S85.

The invention claimed is:

1. A method for visualization of 3D parametric data in a 2D image of a non-planar surface, the method comprising:
 receiving first signals representing 3D surface data representing a non-planar 3D surface of a physical object to be visualized;
 receiving second signals representing a set of 3D parametric data, the 3D parametric data being distinct from the 3D surface data representing the 3D surface of the physical object to be visualized, the set of 3D parametric data including a plurality of voxels in 3D space each associated with at least one parametric value;
 spatially registering the 3D surface data representing the 3D surface of the physical object to be visualized and the 3D parametric data, the registered 3D surface having a plurality of surface elements;
 receiving third signals representing a set of 2D image data representing the 2D image, the set of 2D image data including information about a known camera position and a known camera orientation at which the 2D image was obtained;
 identifying voxels of the set of 3D parametric data corresponding to a set of surface elements of the plurality of surface elements of the 3D surface of the physical object to be visualized, the identifying based at least partly on the spatial registration of the 3D surface data representing the 3D surface of the physical object to be visualized and the 3D parametric data;
 generating a graphical representation of the parametric values of the voxels of the set of 3D parametric data corresponding to the set of surface elements of the 3D surface of the physical object to be visualized by, for each surface element in the set of surface elements, assigning a parametric value of the parametric values based on one or more voxels being closest to the respective surface element, and generating a visual representation based on the assigned parametric value;
 determining a virtual 2D view of the 3D surface of the physical object to be visualized, the virtual 2D view corresponding to the known camera position and the known camera orientation of the 2D image;
 modifying the virtual 2D view with the graphical representation of the parametric values corresponding to the virtual 2D view of the 3D surface of the physical object to be visualized by
 combining the obtained 2D image with at least a part of the virtual 2D view to produce a combined 2D image by at least one of overlaying and underlaying the graphical representation of the parametric values with the obtained 2D image, the obtained 2D image and the graphical representation of the parametric values being visible in the combined 2D image based on the visual representations; and
 providing signals for displaying the combined 2D image.

2. The method of claim 1 wherein the set of 3D parametric data represents 3D radiation dose data.

3. The method of claim 1 wherein the set of 3D parametric data represents 3D positron emission tomography (PET) data.

4. The method of claim 1 wherein the 3D surface data comprises 3D imaging data, and the spatial registration comprises spatially registering the 3D parametric data to 3D imaging data.

5. The method of claim 4 wherein the 3D imaging data comprises computed tomography (CT) imaging data.

6. The method of claim 1 wherein the obtained 2D image comprises an endoscopic image.

7. The method of claim 1 wherein there is a plurality of 2D images that are updated continuously or intermittently in real-time, the virtual 2D view is updated in real-time to correspond to each update of the 2D images, and the combined 2D image is updated in real-time to display the each updated 2D image registered with the graphical representation corresponding to the updated virtual 2D view.

8. The method of claim 1 further comprising determining which voxels corresponding to the 3D surface are visible at the known camera position and the known camera orientation, where voxels that are visible are determined to be visible voxels and voxels that are not visible are determined to be not visible voxels; and wherein the graphical representation includes only the parametric values of the visible voxels.

9. The method of claim 1 wherein the graphical representation of the parametric values comprises at least one of: a set of isolines and a color map.

10. Previously Presented) The method of claim 9 wherein the graphical representation comprises a set of isolines, and generating the set of isolines comprises: determining a set of isosurfaces in the 3D parametric data, each isosurface including voxels of the 3D parametric data having parametric values equal to a defined value or within a defined value range; and determining, for each isosurface, a respective intersection between that isosurface and the 3D surface, each respective intersection defining an isoline corresponding to the respective defined value or defined value range.

11. The method of claim 9 wherein the graphical representation comprises a color map and generating the color map comprises: generating a copy of the 3D surface having a plurality of defined regions; for each region, determining any intersection between that region and any voxels in the 3D parametric data; where there is no voxel in the 3D parametric data intersecting with that region, assign that region to be transparent; where there is at least one intersecting voxel in the 3D parametric data intersecting with that region, assign an opaque color to that region based on the parametric value of the at least one intersecting voxel; wherein any regions assigned an opaque color together define the color map.

12. The method of claim 1, wherein a threshold value is defined for the values of the 3D parametric data, wherein any voxel associated with a parametric value that does not meet the threshold value is rendered in a background color or is rendered transparent in the graphical representation.

13. The method of claim 1, wherein the combining comprises at least one of overlaying and underlaying the obtained 2D image with the at least a part of the updated 2D view.

14. The method of claim 1 wherein the graphical representation of the parametric values is provided for a selected portion of the 3D surface.

15. The method of claim 1 further comprising displaying actual numerical value or values of the parametric value or values for a selected point or portion of the 3D surface.

16. The method of claim 1 wherein the 3D parametric data includes data representative of at least one of a surface property and a subsurface property of the 3D surface.

17. The method of claim 1, wherein the 3D surface is a tissue surface.

18. The method of claim 1, wherein generating the graphical representation of the parametric values of the voxels of the set of 3D parametric data corresponding to the set of surface elements of the 3D surface of the physical object to be visualized comprises: generating a set of isolines for 3D continuous contour lines of the 3D surface data with common isovalues, each isoline corresponding to a subset of the surface elements corresponding to the parametric values of the voxels, for each isoline, assigning a unique color to the subset of the surface elements for the respective isoline, and making opaque the set of isolines using the transparency level, the opaque isolines of the graphical representation of the parametric values being visible in the combined 2D image.

19. The method of claim 1, wherein generating the graphical representation of the parametric values of the voxels of the set of 3D parametric data corresponding to the set of surface elements of the 3D surface of the physical object to be visualized comprises: generating a color map for the 3D surface data the color map having color elements representing the color values of the surface elements corresponding to the parametric values of the voxels of the set of 3D parametric data corresponding to the set of surface elements of the 3D surface of the physical object to be visualized, assigning a scalar value to each surface element of the subset of the parametric values of the voxels, assigning a unique color value to each scalar value of the assigned scalar values, the unique color value not corresponding to a color in the 3D surface of the physical object to be visualized, the unique color values for the color values representing the color elements of the color map, the visual representation having a transparency level defining the color elements representing the surface elements to have a non-zero transparency level, the color elements being visible in the combined 2D image based on the transparency level.

20. The method of claim 1, wherein generating the graphical representation of the parametric values of the voxels of the set of 3D parametric data corresponding to the set of surface elements of the 3D surface of the physical object to be visualized comprises: assigning a scalar value to each surface element of the subset of the surface elements, assigning a unique color value to each scalar value of the assigned scalar values, the unique color values providing the color values of the graphical representation, the visual representation having a transparency level defining the color values representing the parametric values of the voxels to have a non-zero transparency level, the color values being visible in the combined 2D image based on the transparency level.

21. The method of claim 1, the graphical representation of the parametric values having a transparency mask causing a portion of the virtual 2D view to be rendered transparent in the combined 2D image.

22. The method of claim 1, the visual representation having a color value and a transparency level based on the respective assigned parametric value.

23. A system for visualization of 3D parametric data in a 2D image of a non-planar surface, the system comprising: a processor configured to execute computer-executable instructions to carry out the method of any one of claims 1 to 16; and a display for displaying the 2D image registered with the graphical representation of the parametric values of the voxels corresponding to the virtual 2D view.

24. The system of claim 23 further comprising a camera for capturing the 2D image.

25. The system of claim 23 wherein the system is an imaging workstation.

* * * * *